(12) United States Patent
Showe et al.

(10) Patent No.: US 9,920,375 B2
(45) Date of Patent: Mar. 20, 2018

(54) BIOMARKERS IN PERIPHERAL BLOOD MONONUCLEAR CELLS FOR DIAGNOSING OR DETECTING LUNG CANCERS

(71) Applicant: THE WISTAR INSTITUTE OF ANATOMY AND BIOLOGY, Philadelphia, PA (US)

(72) Inventors: Louise C. Showe, Media, PA (US); Michael Showe, Media, PA (US); Andrew V. Kossenkov, Huntington Valley, PA (US); Elena Nikonova, Swarthmore, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 14/719,826

(22) Filed: May 22, 2015

(65) Prior Publication Data

US 2015/0252441 A1 Sep. 10, 2015

Related U.S. Application Data

(62) Division of application No. 13/127,161, filed as application No. PCT/US2009/063603 on Nov. 6, 2009, now Pat. No. 9,068,974.

(60) Provisional application No. 61/112,744, filed on Nov. 8, 2008.

(51) Int. Cl.
   *C12Q 1/68* (2006.01)
   *G01N 33/50* (2006.01)
   *G01N 33/574* (2006.01)

(52) U.S. Cl.
   CPC ......... *C12Q 1/6886* (2013.01); *C12Q 1/6809* (2013.01); *C12Q 1/6883* (2013.01); *G01N 33/5091* (2013.01); *G01N 33/5094* (2013.01); *G01N 33/57423* (2013.01); *C12Q 2600/112* (2013.01); *C12Q 2600/118* (2013.01); *C12Q 2600/16* (2013.01); *C12Q 2600/178* (2013.01); *G01N 2800/122* (2013.01)

(58) Field of Classification Search
   None
   See application file for complete search history.

(56) References Cited

U.S. PATENT DOCUMENTS

| | | | |
|---|---|---|---|
| 5,079,147 | A | 1/1992 | Showe et al. |
| 6,040,138 | A | 3/2000 | Lockhart et al. |
| 7,640,114 | B2 | 12/2009 | Showe et al. |
| 2004/0175732 | A1 | 9/2004 | Rana |
| 2006/0105360 | A1 | 5/2006 | Croce et al. |
| 2006/0134639 | A1 | 6/2006 | Huffel et al. |
| 2006/0223127 | A1 | 10/2006 | Yip et al. |
| 2007/0099196 | A1 | 5/2007 | Kauppinen et al. |
| 2007/0299030 | A1* | 12/2007 | Dmitrovsky .......... C12N 15/111 514/44 A |
| 2008/0076674 | A1 | 3/2008 | Litman et al. |
| 2008/0182245 | A1 | 7/2008 | Brown et al. |
| 2010/0184046 | A1 | 7/2010 | Klass et al. |
| 2010/0255486 | A1 | 10/2010 | Showe et al. |

FOREIGN PATENT DOCUMENTS

| | | |
|---|---|---|
| WO | WO-2004/105573 | 12/2004 |
| WO | WO-2008/073923 | 6/2008 |
| WO | WO-2009/075799 | 6/2009 |

OTHER PUBLICATIONS

Notice of Allowance with Examiner Initiated Interview Summary issued on parent U.S. Appl. No. 13/127,161, dated Feb. 25, 2015.
Response to Office Action dated Oct. 9, 2014 issued on parent U.S. Appl. No. 13/127,161, filed Jan. 7, 2015.
Office Action issued on Parent U.S. Appl. No. 13/127,161, dated Oct. 9, 2014.
Examiner Initiated Interview Summary issued on parent U.S. Appl. No. 13/127,161, dated Mar. 26, 2014.
Amendment filed with Request for Continued Examination in parent U.S. Appl. No. 13/127,161 with Applicant Summary of Interview with Examiner, dated Mar. 17, 2014.
Applicant Initiated Interview Summary issued on parent U.S. Appl. No. 13/127,161, dated Feb. 25, 2014.
Response to Final Office Action dated Dec. 17, 2013 issued on parent U.S. Appl. No. 13/127,161, filed Feb. 19, 2014.
Final Office Action issued on parent U.S. Appl. No. 13/127,161, dated Dec. 17, 2013.
Response to Office Action dated Aug. 12, 2013 issued on parent U.S. Appl. No. 13/127,161, filed Nov. 12, 2013.
Office Action issued on parent U.S. Appl. No. 13/127,161, dated Aug. 12, 2013.
Response to Restriction Requirement dated May 10, 2013 issued on parent U.S. Appl. No. 13/127,161, filed Jul. 3, 2013.
Restriction Requirement issued on parent U.S. Appl. No. 13/127,161, dated May 10, 2013.
Betel D, Wilson M, Gabow A, Marks DS, Sander C., The microRNA.org resource: targets and expression. Nucleic Acids Research, 36(Database issue):D149-53. Epub (Dec. 23, 2007).
Esquela-Kerscher and Slack, Oncomirs—microRNAs with a role in cancer, Nature Reviews. Cancer, 6(4):259-269 (Apr. 2006).
Kari L, et al, Classification and prediction of survival in patients with the leukemic phase of cutaneous T cell lymphoma, Journal of Experimental Medicine, 197(11):1477-88 (Jun. 2003).

(Continued)

*Primary Examiner* — Addison D Ault
(74) *Attorney, Agent, or Firm* — Howson & Howson LLP

(57) ABSTRACT

Methods and compositions are provided for diagnosing or detecting a condition, e.g., lung disease in a mammalian subject by use of a micro-RNA expression level or an expression level profile of multiple miRNA in the peripheral blood mononuclear cells (PBMC) of the subject which is characteristic of COPD or NSCLC. Detection of changes in expression in specific miRNA biomarkers from that of a reference sample or miRNA expression profile are correlated with non-small cell lung cancer (NSCLC) and/or COPD and permit differentiation among healthy subjects, subjects with COPD and subjects with adenocarcinoma or squamous cell carcinoma.

3 Claims, 8 Drawing Sheets

(56) References Cited

OTHER PUBLICATIONS

Karube Y et al Reduced expression of Dicer associated with poor prognosis in lung cancer patients, Cancer Science, 96(2):111-5 (Feb. 2005).
Liang Y, et al, Characterization of microRNA expression profiles in normal human tissues, BMC Genomics, 8:166 (Jun. 2007).
McManus, MicroRNAs and cancer, Seminars in Cancer Biology, 13:253-258 (Aug. 2003).
Nebozhyn M, et al, Quantitative PCR on 5 genes reliably identifies CTCL patients with 5% to 99% circulating tumor cells with 90% accuracy, Blood, 107(8):3189-96 (Apr. 2006).
Yanaihara N. et al, Unique microRNA molecular profiles in lung cancer diagnosis and prognosis, Cancer Cell, 9(3):189-98 (Mar. 2006).
International Search Report, dated Mar. 5, 2010, issued in corresponding International Patent Application No. PCT/US09/63603.
Written Opinion, dated Mar. 5, 2010, issued in corresponding International Patent Application No. PCT/US09/63603.
International Preliminary Report on Patentability, dated May 10, 2011, issued in corresponding International Patent Application No. PCT/US09/63603.

\* cited by examiner

FIG. 3

| Symbol | AC-E | SCC-E | COPD | S | NS | Max ratio | Between | COPD/(AC+SCC) |
|---|---|---|---|---|---|---|---|---|
| miR-142-5p | 0.0600051 | 0.0290208 | 0.203059 | 0.157559 | 0.295955 | 10.19803038 | NS/SCC | 4.561796062 |
| miR-328 | 0.014838 | 0.00691834 | 0.0343394 | 0.0235072 | 0.0263699 | 4.963531714 | COPD/SCC | 3.15672581 |
| miR-127 | 0.00952596 | 0.00691834 | 0.0311201 | 0.0102097 | 0.00977145 | 4.498203326 | COPD/SCC | 3.784910273 |
| miR-221 | 0.157858 | 0.0802051 | 0.354122 | 0.1705 | 0.204587 | 4.415205517 | COPD/SCC | 2.975026369 |
| miR-148b | 0.0141785 | 0.00691834 | 0.0261208 | 0.0186393 | 0.0213643 | 3.775587786 | COPD/SCC | 2.476276068 |
| miR-148a | 0.0210286 | 0.0113596 | 0.0402991 | 0.0260956 | 0.0306458 | 3.547580901 | COPD/SCC | 2.488505073 |
| miR-151 | 0.0679291 | 0.0266771 | 0.0925392 | 0.0545672 | 0.0522329 | 3.468862807 | COPD/SCC | 1.956303075 |
| miR-103 | 0.122071 | 0.0653881 | 0.22518 | 0.163945 | 0.169704 | 3.44374588 | COPD/SCC | 2.402444053 |
| miR-335 | 0.0176603 | 0.00693757 | 0.0227919 | 0.0140475 | 0.0198688 | 3.28528577 | COPD/SCC | 1.853160457 |
| miR-126 | 0.929008 | 0.404161 | 1.27684 | 0.627865 | 0.731775 | 3.159236047 | COPD/SCC | 1.915496085 |
| miR-18a | 0.0192476 | 0.010352 | 0.0314102 | 0.0168627 | 0.0245625 | 3.034215611 | COPD/SCC | 2.122339491 |
| let-7d | 0.0120981 | 0.00781318 | 0.0235644 | 0.0194638 | 0.0169373 | 3.015980689 | COPD/SCC | 2.366939745 |
| miR-186 | 0.135957 | 0.0705185 | 0.209598 | 0.114075 | 0.154939 | 2.972241327 | COPD/SCC | 2.030245719 |
| miR-425-5p | 0.110645 | 0.0537604 | 0.150726 | 0.0829696 | 0.0970802 | 2.803662175 | COPD/SCC | 1.833589408 |
| miR-331 | 0.0850212 | 0.0397951 | 0.110559 | 0.0755003 | 0.0980854 | 2.778206362 | COPD/SCC | 1.771547466 |
| miR-17-5p | 0.0691886 | 0.0356664 | 0.097036 | 0.0609016 | 0.0615906 | 2.730469013 | COPD/SCC | 1.857536598 |
| miR-15b | 0.237097 | 0.144543 | 0.387471 | 0.233463 | 0.340782 | 2.680662502 | COPD/SCC | 2.030557594 |
| let-7a | 0.0291321 | 0.0217567 | 0.0578985 | 0.0422533 | 0.0431993 | 2.661180234 | COPD/SCC | 2.275490874 |
| miR-451 | 0.0080564 | 0.00691834 | 0.0183519 | 0.00691834 | 0.00726302 | 2.652644999 | COPD/SCC | 2.451047564 |
| miR-31 | 0.0328979 | 0.0126015 | 0.0216321 | 0.0230106 | 0.0277743 | 2.610633655 | AC/SCC | -1.051663962 |
| miR-486 | 0.0550382 | 0.0232255 | 0.0567314 | 0.0262533 | 0.022564 | 2.514243928 | COPD/NS | 1.449750012 |
| miR-20b | 0.0206978 | 0.0177266 | 0.0433055 | 0.0212321 | 0.0263255 | 2.442967066 | COPD/SCC | 2.254062523 |
| miR-30e-3p | 0.0304728 | 0.0224669 | 0.0548804 | 0.0419528 | 0.0479109 | 2.442722405 | COPD/SCC | 2.073317378 |
| miR-423 | 0.0195291 | 0.011077 | 0.0269726 | 0.0208761 | 0.0261811 | 2.435009479 | COPD/SCC | 1.762563672 |
| miR-199a | 0.018938 | 0.00834427 | 0.0200346 | 0.0158926 | 0.0177919 | 2.401000926 | COPD/SCC | 1.468690105 |
| miR-93 | 0.268794 | 0.180717 | 0.433104 | 0.307926 | 0.350449 | 2.396586929 | COPD/SCC | 1.927000674 |
| miR-28 | 0.0477484 | 0.0277274 | 0.0664377 | 0.0552092 | 0.0547635 | 2.396102772 | COPD/SCC | 1.760503367 |
| miR-21 | 0.490175 | 0.322906 | 0.74624 | 0.583815 | 0.627203 | 2.311013112 | COPD/SCC | 1.835585876 |
| miR-222 | 0.278372 | 0.135495 | 0.3131 | 0.192663 | 0.245632 | 2.310786376 | COPD/SCC | 1.513046462 |
| miR-30e-5p | 0.0418573 | 0.0300305 | 0.0229761 | 0.0480601 | 0.052231 | 2.273275273 | NS/COPD | -1.564403881 |
| miR-594 | 0.245071 | 0.202272 | 0.284763 | 0.154523 | 0.125299 | 2.272667779 | COPD/NS | 1.273130461 |
| miR-340 | 0.0156269 | 0.0114176 | 0.0258377 | 0.0143403 | 0.0200459 | 2.262971202 | COPD/SCC | 1.910754497 |
| miR-126 | 0.179874 | 0.090728 | 0.204235 | 0.149202 | 0.166536 | 2.25106913 | COPD/SCC | 1.509486257 |
| miR-130a | 0.0366482 | 0.0201687 | 0.0446426 | 0.0233074 | 0.0288036 | 2.213459469 | COPD/SCC | 1.571454972 |
| miR-25 | 0.0534095 | 0.0338517 | 0.0709262 | 0.0541929 | 0.0745367 | 2.201859877 | NS/SCC | 1.625606799 |
| miR-660 | 0.0409935 | 0.0208929 | 0.0459857 | 0.0281123 | 0.0400734 | 2.201020442 | COPD/SCC | 1.486132656 |
| miR-181d | 0.021877 | 0.0312779 | 0.0475458 | 0.0233344 | 0.0249679 | 2.173323582 | COPD/AC | 1.788952665 |
| miR-125a | 0.0496463 | 0.0275318 | 0.0573164 | 0.0579652 | 0.0440436 | 2.105390857 | S/SCC | 1.485302178 |
| miR-27b | 0.00742293 | 0.00691834 | 0.0144718 | 0.0101057 | 0.0095459 | 2.091802369 | COPD/SCC | 2.018203409 |
| miR-532 | 0.0198266 | 0.0162148 | 0.0337929 | 0.0243492 | 0.0275959 | 2.084077509 | COPD/SCC | 1.875226822 |
| miR-24 | 0.924117 | 0.612544 | 1.27619 | 0.883755 | 0.920406 | 2.083425844 | COPD/SCC | 1.660990941 |
| miR-181b | 0.0458954 | 0.0492651 | 0.0860774 | 0.0456634 | 0.0612058 | 1.885041412 | COPD/S | 1.809099364 |
| miR-22 | 0.0254301 | 0.0148072 | 0.0246889 | 0.0171898 | 0.0202411 | 1.717414501 | AC/SCC | 1.227164845 |

AC-E = Early Stage Carcinoma
SCC-E = Early Stage Squamous Cell Carcinoma
COPD = Chronic Obstructive Pulmonary Disease
S = Smoker
NS = Never Smoker

BIOMARKERS IN PERIPHERAL BLOOD MONONUCLEAR CELLS FOR DIAGNOSING OR DETECTING LUNG CANCERS

CROSS-REFERENCE TO RELATED APPLICATIONS

This application is a divisional of U.S. patent application Ser. No. 13/127,161, filed May 2, 2011, which is a national stage of International Patent Application No. PCT/US2009/063603, filed Nov. 6, 2009, which claims the benefit of the priority of U.S. Provisional Patent Application No. 61/112,744, filed Nov. 8, 2008, which applications are incorporated herein by reference.

BACKGROUND OF THE INVENTION

Lung cancer is the most common worldwide cause of cancer mortality. Non-small cell lung cancer (NSCLC) is a highly lethal disease with cure only possible by early detection followed by surgery. Unfortunately, at the time of diagnosis only 15% of patients with lung cancer have localized disease. Field cancerization in which the lung epithelium becomes mutagenized following exposure to cigarette smoke makes it difficult to identify genetic changes that differentiate smokers from smokers with early lung cancer.

One of the most important long-term goals in improving lung cancer survival is to detect malignant tumors in high-risk patients, primarily smokers and former smokers, who represent the majority of all lung cancer cases, at an early stage, while they are still surgically resectable. Although most patients with lung cancer are smokers or ex-smokers, the actual incidence of lung cancer in this group is quite small (<0.2%). Various studies have demonstrated that the incidence of lung cancer in male cigarette smokers ranged from 0.16% (in Caucasians) to 0.26% (in African Americans). Another high-risk population is subjects with lung nodules of unknown etiology, as identified on screening chest X-rays, computerized axial tomography (CT) scans, low dose spiral CT scans, or incidentally. Currently, the only way to differentiate benign from malignant nodules is an invasive biopsy, surgery, or prolonged observation with repeated scanning.

While these methods may identify non-calcified pulmonary nodules in approximately 30% of screened smokers and ex-smokers (with a range of 13-51% of patients on prevalence screen; 2-13% on annual screen), only a small number are found to be lung cancers (0.4 to 2.7%). Thus, about 3 to 12% of subjects with detected non-calcified nodules prompt an invasive diagnostic workup. The high false positive rate of CT scanning requires patients to undergo extensive follow-up investigations with serial CT, positron emission tomography (PET scan), and/or biopsy. Studies indicate that 20-55% of patients undergoing surgical lung biopsy for indeterminate lung nodules are subsequently found to have benign disease.

One established and validated method to achieve the goal of genetic diagnosis has been the use of microarray signatures from tumor tissue. Peripheral blood mononuclear cells (PBMC) profiles can be used to diagnose and classify systemic diseases, including cancer, and to monitor therapeutic response. The validity of using PBMC gene expression profiles in patients with cancer has been previously reported in the use of microarrays to compare PBMC from patients with late stage renal cell carcinoma compared to normal controls. A 37 gene classifier has been developed for detecting early breast cancer from peripheral blood samples with 82% accuracy. Another study identified gene expression profiles in the PBMC of colorectal cancer patients that could be correlated with response to therapy.

While the effect of chronic obstruction pulmonary disease (COPD) on PBMC gene expression is relatively unstudied to date, there are some limited reports about the effect of cigarette smoke. Exposure of peripheral blood lymphocytes (PBL) ex vivo to cigarette smoke induced many changes in gene expression. Changes could be detected in the transcriptosome of blood neutrophils in COPD patients versus normals. Gene expression in airway epithelia of smokers, ex-smokers and non-smokers has been compared. Although many clinical manifestations of smoking rapidly returned to normal after smoking cessation, there was a subset of genes whose expression remained altered.

MicroRNAs (miRNAs) are a large group of ribonucleic acid sequences, isolated and identified from insects, microorganisms, humans, animals and plants, which are reported in databases including that of The Wellcome Trust Sanger Institute (http://miRNA.sanger.ac.uk/sequences/). These miRNAs are about 22 nucleotides in length and arise from longer precursors, which are transcribed from non-protein-encoding genes. The precursors form structures that fold back on themselves in self-complementary regions. Relatively little is known about the functional role of miRNAs and even less on their targets. It is believed that miRNA molecules interrupt or suppress gene translation through precise or imprecise base-pairing with their targets (US Published Patent Application No. 2004/0175732). Bioinformatics analyses suggest that any given miRNA may bind to and alter the expression of up to several hundred different genes; and a single gene may be regulated by several miRNAs. The complicated interactive regulatory networks among miRNAs and target genes have been noted to make it difficult to accurately predict which genes will actually be misregulated in response to a given miRNA. Expression levels of certain miRNAs have been associated with various cancers (Esquela-Kerscher and Slack, 2006 Nat. Rev. Cancer, 6(4):259-269; McManus 2003 Seminars in Cancer Biology, 13:253-258; Karube Y et al 2005 Cancer Sci, 96(2):111-5; Yanaihara N. et al 2006 Cancer Cell, 9(3):189-98).

There remains a need in the art for new and effective tools to facilitate early diagnoses of various lung cancers, as well as less invasive diagnostic tests that could more accurately diagnose malignant disease in patients from other non-malignant diseases and would reduce unnecessary diagnostic surgery, biopsies, PET scans, and/or repeated CT scans.

SUMMARY OF THE INVENTION

In one embodiment, a method of diagnosing or detecting, detecting or assessing a condition in a mammalian subject is provided. This method comprises detecting in a biological sample of the subject, or from an miRNA expression profile generated from the sample, the expression level of an miRNA nucleic acid sequence identified in Table 1. The miRNA expression level or miRNA expression profile in the subject's sample is compared to a reference miRNA standard. A change in expression of the subject's sample miRNA from that in the reference miRNA standard indicates a diagnosis, detection, discrimination or prognosis of a selected condition. The condition detected includes a lung cancer, such as a type or stage of a non-small cell lung cancer, chronic obstructive pulmonary disease (COPD), and benign lung nodules. In certain embodiments, the condition detected or discriminated is a lung cancer in a subject post surgical resection of a tumor. This condition can be monitored by comparing an miRNA or miRNA profile or pattern obtained before surgery with the post-surgical levels of the miRNA. In certain embodiments, the biological sample is whole blood, peripheral blood mononuclear cells, plasma or serum.

In another aspect, a method of diagnosing or detecting or assessing a lung disease in a mammalian subject is provided, comprising detecting in a sample of the subject's peripheral blood mononuclear cells (PBMC), or from an miRNA expression profile generated from the sample, the expression level of at least one of the miRNA nucleic acid sequences of Table 1. In another embodiment, the same method is performed using a different sample, e.g., whole blood. The miRNA expression level of the specified miRNA in the sample is compared to an average or standard expression level of the same miRNA in a reference sample or profile. A change in expression of at least one of these miRNA from that in the reference indicates a diagnosis of non small cell lung cancer (NSCLC) or chronic obstructive pulmonary disease (COPD). In one embodiment the NSCLC is adenocarcinoma or squamous cell carcinoma. In another embodiment the NSCLC is early stage (I or II) adenocarcinoma or early stage (I or II) squamous cell carcinoma. In another embodiment, the change in expression of the miRNA is useful to monitor patients who have had a cancerous lung tumor surgically removed by comparing the miRNA with the same miRNA pre-surgery. In certain embodiments of these methods, the reference standard utilized is a standard or profile derived from the same sample, e.g., PBMC or whole blood, of a reference human subject or an average of multiple subjects with a particular physical condition, as defined herein.

In another aspect, a method of diagnosing or detecting a lung disease or condition in a mammalian subject is provided, comprising detecting in a sample of the subject's peripheral blood mononuclear cells (PBMC), or from an miRNA expression profile generated from the sample, the expression level of at least one of the miRNA nucleic acid sequences hsa-miR-148a, hsa-miR-142-5p, hsa-miR-221, hsa-miR-let-7d, has-miR-328, hsa-miR-let-7a, hsa-miR-let-7c, hsa-miR-34a, hsa-miR-202, hsa-miR-769-5p, and hsa-miR-642. In another embodiment, the same method is performed using a different sample, e.g., whole blood. The miRNA expression level of the specified miRNA in the sample is compared to an average or standard expression level of the same miRNA in a reference sample or profile. A change in expression of at least one of these miRNA from that in the reference is indicative of a non small cell lung cancer (NSCLC) or chronic obstructive pulmonary disease (COPD). In one embodiment the NSCLC is adenocarcinoma or squamous cell carcinoma. In another embodiment the NSCLC is early stage (I or II) adenocarcinoma or early stage (I or II) squamous cell carcinoma. In certain embodiments of these methods, the reference standard utilized is a standard or profile derived from same sample, e.g., the PBMC or whole blood, of a reference human subject or an average of multiple subjects with a particular physical condition, as defined below.

In another aspect, methods for diagnosing or detecting adenocarcinoma are accomplished by detecting in a sample of a subject's PBMC changes in certain miRNA expression levels or miRNA expression profiles as identified below from those of a reference standard or profile. In another embodiment, the same method is performed using a different sample, e.g., whole blood.

In another aspect, methods for diagnosing or detecting squamous cell carcinoma are accomplished by detecting in a sample of a subject's PBMC changes in certain miRNA expression levels or miRNA expression profiles as identified below from those of a reference standard or profile. In another embodiment, the same method is performed using a different sample, e.g., whole blood.

In another aspect, methods for diagnosing or detecting chronic obstructive pulmonary disease are accomplished by detecting in a sample of a subject's PBMC changes in certain miRNA expression levels or miRNA expression profiles as identified below from those of a reference standard or profile. In another embodiment, the same method is performed using a different sample, e.g., whole blood.

In another aspect, a composition, diagnostic reagent, kit, or microarray for diagnosing or detecting a condition, e.g., a lung disease, in a mammalian subject employs at least two ligands, e.g., nucleic acid primers, wherein each ligand hybridizes to or complexes with or identifies a single different miRNA nucleic acid sequence from among two or more miRNAs identified in Table 1 and FIG. 3 as characteristic of a particular condition, e.g., lung disease. In certain embodiments, the primers are immobilized on a substrate.

In another aspect, a composition, kit, or microarray for diagnosing or detecting a lung disease in a mammalian subject contains at least two nucleic acid primers, wherein each the primer hybridizes with a single different miRNA nucleic acid sequence. The miRNA are characteristic of a particular condition, e.g., lung disease and include one or more miRNA selected from: hsa-miR-148a, hsa-miR-142-5p, hsa-miR-221, hsa-miR-let-7d, hsa-miR-let-7a, hsa-miR-328, hsa-miR-let-7c, hsa-miR-34a, hsa-miR-202, hsa-miR-769-5p, hsa-miR-642.

In another aspect, the composition, kit, or microarray employs antibodies, fragments or probes that identify one or more of the miRNAs disclosed herein.

The methods and compositions described herein allow the physician to distinguish between non-cancerous conditions, such as COPD or benign lung nodules, from lung cancer, such as NSCLC. The methods and compositions described herein allow the physician to monitor the status of a lung cancer patient post-surgical resection of a tumor.

Other aspects and advantages of these compositions and methods are described further in the following detailed description of the preferred embodiments thereof.

BRIEF DESCRIPTION OF THE DRAWINGS

FIG. 3 is a table of data obtained from a hierarchical clustering of 43 peripheral blood mononuclear cells-derived miRNAs differentially expressed in RNA pools. Each listed miRNA is identified by name, as reported in Table 1, and was expressed at Ct≤31 and had about 2-fold difference between any pair of pooled peripheral blood mononuclear cells samples. Hierarchical clustering (not shown) was done using normalized Euclidean distance for samples and correlation similarity metric for miRNAs. The data from the clustering are reported in the Figure using arbitrary expression units under each subject population. COPD represents a population having chronic obstructive pulmonary disease (predominantly former smokers); AC-E represents early stage (stage I+II) adenocarcinoma; SCC-E represents early stage I and II squamous cell carcinoma; S represents a population of smokers without disease; NS represents a population of healthy subjects who have never smoked. "Max ratio" represents the fold difference in expression between the two groups furthest apart in expression, adjacent the identity of the two groups. The final column is the ratio between expression in COPD vs. expression in all NSCLC subjects. For miRNA expression, a difference of 1.2 fold and above is considered significant between two groups. Negative numbers are indicative of upregulation of the miRNA in the NSCLC subjects compared to COPD. Positive numbers are indicative of downregulation of the miRNA in the NSCLC subjects compared to COPD patients. Each PBMC-derived miRNA was differentially expressed in 5 RNA pools. Each miRNA was expressed at Ct≤31 and had at least 2-fold difference between any pair of pooled PBMC samples. Hierarchical clustering was done using normalized Euclidean distance for samples and correlation similarity metric for miRNAs (not shown).

DETAILED DESCRIPTION OF THE INVENTION

Figure 1A:
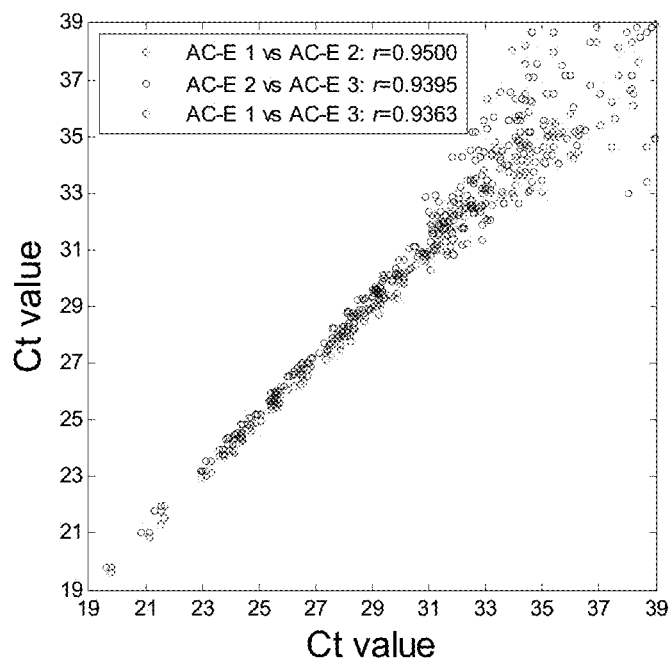
FIG. 1A shows TaqMan® Low Density Array (TLDA) reproducibility and sensitivity based on correlation analyses of miRNA expression in three technical replicates of an early stage adenocarcinoma (AC-E) sample. This graph shows Spearman correlation (r) between the replicates based on cycle threshold (Ct) less than 39.

The methods and compositions described herein apply miRNA expression technology to blood screening for the detection, diagnosis, and monitoring of response to treatment of a condition, such as a lung disease. In certain embodiments, the lung disease is an NSCLC or COPD. The compositions and methods described herein permit the diagnosis or detection of a condition or disease or its stage generally, and lung cancers and COPD particularly, by determining changes in a characteristic miRNA or miRNA expression profile derived from a biological sample, including in various embodiments, whole blood, peripheral blood mononuclear cells (PBMC) or peripheral blood lymphocytes (PBL) of a mammalian, preferably human, subject. The miRNA expression of a single miRNA or a profile of two or more miRNA identified below is established by comparing the profiles of numerous subjects of the same class (e.g., patients with a certain type and stage of lung cancer or COPD, or a mixture of types and stages) with numerous subjects of a class from which these individuals must be distinguished in order to provide a useful diagnosis.

These methods of lung disease screening employ compositions suitable for conducting a simple and cost-effective and non-invasive blood test using miRNA expression profiling that could alert the patient and physician to obtain further studies, such as a chest radiograph or CT scan, in much the same way that the prostate specific antigen is used to help diagnose and follow the progress of prostate cancer. The miRNA expression levels and profiles described herein provide the basis for a variety of classifications related to this diagnostic problem. The application of these comparative levels and profiles provides overlapping and confirmatory diagnoses of the type of lung disease, beginning with the initial test for malignant vs. non-malignant disease.

I. Definitions

"Patient" or "subject" as used herein means a mammalian animal, including a human, a veterinary or farm animal, a domestic animal or pet, and animals normally used for clinical research. More specifically, the subject of these methods and compositions is a human.

"Reference" level, standard or profile as used herein refers to the source of the reference miRNA. In one embodiment, the reference miRNA standard is obtained from biological samples selected from a reference human subject or population having a non-small cell lung cancer (NSCLC). For example, in one embodiment, the reference standard utilized is a standard or profile derived from the PBMC of a reference human subject or population of human subjects with squamous cell carcinoma or an average of multiple subjects with squamous cell carcinoma. In certain embodiments, the reference standard utilized is a standard or profile derived from the PBMC of a reference human subject, or an average of multiple subjects, with early stage squamous cell carcinoma. In another embodiment, the reference standard is a standard or profile derived from the PBMC of a reference human subject, or an average of multiple subjects, with adenocarcinoma. In another embodiment, the reference standard is a standard or profile derived from the PBMC of a reference human subject, or an average of multiple subjects, with early stage adenocarcinoma.

In another embodiment, the reference miRNA standard is obtained from biological samples selected from a reference human subject or population having COPD. For example, the reference standard is a standard or profile derived from the PBMC of a reference human subject, or an average of multiple subjects, with COPD. In one embodiment, the reference miRNA standard is obtained from biological samples selected from a reference human subject or population who are healthy and have never smoked. For example, the reference standard is a standard or profile derived from the PBMC of a reference human subject, or an average of multiple subjects, who are healthy and have never smoked. In one embodiment, the reference miRNA standard is obtained from biological samples selected from a reference human subject or population who are former smokers or current smokers with no disease. For example, the reference standard is a standard or profile derived from the PBMC of a reference human subject, or an average of multiple subjects, who are former smokers or current smokers with no disease.

In one embodiment, the reference miRNA standard is obtained from biological samples selected from a reference human subject or population having benign lung nodules. For example, the reference standard is a standard or profile derived from the PBMC of a reference human subject, or an average of multiple subjects, who have benign lung nodules. In one embodiment, the reference miRNA standard is obtained from biological samples selected from a reference human subject or population following surgical removal of an NSCLC tumor. In one embodiment, the reference miRNA standard is obtained from biological samples selected from a reference human subjects or population prior to surgical removal of an NSCLC tumor. In one embodiment, the reference miRNA standard is obtained from biological samples selected from the same subject who provided a temporally earlier biological sample. In another embodiment, the reference standard is a combination of two or more of the above reference standards.

The reference standard, in various embodiments, is a mean, an average, a numerical mean or range of numerical means, a numerical pattern, a graphical pattern or an miRNA or mRNA or gene expression profile derived from a reference subject or reference population. Selection of the particular class of reference standards, reference population, miRNA levels or profiles depends upon the use to which the diagnostic/monitoring methods and compositions are to be put by the physician.

"Sample" or "Biological Sample" as used herein means any biological fluid or tissue that contains immune cells and/or cancer cells. In one embodiment, a suitable sample is whole blood. In another embodiment, a suitable sample for use in the methods described herein includes peripheral blood, more specifically peripheral blood mononuclear cells. Other useful biological samples include, without limitation, whole blood, plasma, serum, saliva, urine, synovial fluid, bone marrow, cerebrospinal fluid, vaginal mucus, cervical mucus, nasal secretions, sputum, semen, amniotic fluid, bronchoalveolar lavage fluid, and other cellular exudates from a subject suspected of having a lung disease. Such samples may further be diluted with saline, buffer or a physiologically acceptable diluent. Alternatively, such samples are concentrated by conventional means. It should be understood that the use or reference throughout this specification to any one biological sample is exemplary only. For example, where in the specification the sample is referred to as PBMC, it is understood that other samples, e.g., whole blood, plasma, etc., may also be employed in the same manner.

"Immune cells" as used herein means B-lymphocytes, T-lymphocytes, NK cells, macrophages, mast cells, monocytes and dendritic cells.

As used herein, the term "condition" refers to the absence (healthy condition) or presence of a disease including a lung disease, a lung cancer, the presence of benign nodules or benign tumor growths in the lung, chronic obstructive pulmonary disease (with or without associated cancer), the existence of a cancerous lung tumor prior to surgery, the post-surgical condition after removal of a cancerous lung tumor. Where specified, any of such conditions can be associated with smoking or not-smoking.

As used herein, the term "lung disease" refers to a lung cancer or chronic obstructive pulmonary disease, or the presence of lung nodules or lung lesions due to smoking or some other adverse even in the lung tissue.

As used herein the term "cancer" refers to or describes the physiological condition in mammals that is typically characterized by unregulated cell growth. More specifically, as used herein, the term "cancer" means any lung cancer. In one embodiment, the lung cancer is non-small cell lung cancer (NSCLC). In a more specific embodiment, the lung cancer type is lung adenocarcinoma (AC). In another embodiment, the lung cancer type is lung squamous cell carcinoma (SCC). In another embodiment, the lung cancer is an "early stage" (I or II) NSCLC. In still another embodiment, the lung cancer is a "late stage" (III or IV) NSCLC. In still another embodiment, the lung cancer is a mixture of early and late stages and types of NSCLC.

The term "tumor," as used herein, refers to all neoplastic cell growth and proliferation, whether malignant or benign, and all pre-cancerous and cancerous cells and tissues.

By "therapeutic reagent" or "regimen" is meant any type of treatment employed in the treatment of cancers with or without solid tumors, including, without limitation, chemotherapeutic pharmaceuticals, biological response modifiers, radiation, diet, vitamin therapy, hormone therapies, gene therapy, surgical resection, etc.

By "specified miRNAs" as used herein is meant those miRNAs the expression of which changes (either in an up-regulated or down-regulated manner) characteristically in the presence of a condition such as lung disease. In one embodiment, the specified miRNAs are those reported in Table 1 and FIG. 3. A statistically significant number of such informative miRNAs that form a suitable miRNA expression profile for use in the methods and compositions is determined based upon the ability of same to discriminate between two or more of the tested reference populations.

The term "statistically significant number of miRNAs" in the context of this invention differs depending on the degree of change in miRNA expression observed. The degree of change in miRNA expression varies with the condition, such as type of lung disease or cancer and with the size or spread of the cancer or solid tumor. The degree of change also varies with the immune response of the individual and is subject to variation with each individual. The degree of change in expression of the specified miRNAs varies with the type of disease diagnosed, e.g., COPD or NSCLC, and with the size or spread of the cancer or solid tumor. The degree of change also varies with the immune response of the individual and is subject to variation with each individual. For example, in one embodiment of this invention, a change at or greater than a 1.2 fold increase or decrease in expression of a miRNA or more than two such miRNA, or even 3 to about 43 characteristic miRNA, is statistically significant. In another embodiment, a larger change, e.g., at or greater than 1.5 fold, greater than 1.7 fold or greater than 2.0 fold increase or decrease in expression of a miRNA or more than two such miRNA, or even 3 to about 43 characteristic miRNA, is statistically significant. This is particularly true for cancers without solid tumors. Still alternatively, if a single miRNA is profiled as up-regulated or expressed significantly in cells which normally do not express the miRNA, such up-regulation of a single miRNA may alone be statistically significant. Conversely, if a single miRNA is profiled as down-regulated or not expressed significantly in cells which normally do express the miRNA, such down-regulation of a single miRNA may alone be statistically significant.

Thus, the methods and compositions described herein contemplate examination of the expression level or profile of from 1 to about 50 miRNA in a single profile (see Table 1). In one embodiment, a significant change in the expression level of one of the identified miRNA can be diagnostic of a condition, e.g., lung disease. In another embodiment, a significant change in the expression level of two of the identified miRNAs can indicate a condition, e.g., a lung disease. In another embodiment, a significant change in the expression level of three of the identified miRNAs can be diagnostic of a lung disease or indicate another condition. In another embodiment, a significant change in the expression level of four or more of the identified miRNAs can be diagnostic of a lung disease or indicate another condition. In another embodiment, a significant change in the expression level of at least 5, at least 6, at least 7, at least 8, at least 9 or at least 10 of the identified miRNAs can be diagnostic of a lung disease or indicate another condition. In another embodiment, a significant change in the expression level of about 15 of the identified miRNAs can be diagnostic of a lung disease or indicate another condition. In another embodiment, a significant change in the expression level of about 20 to 40 of the identified miRNAs can be diagnostic of a lung disease or indicate another condition. Still other numbers of miRNA changes within the specifically identified miRNA can be used in diagnosis of lung disease or indicate another condition as taught herein.

The term "microarray" refers to an ordered arrangement of hybridizable array elements. In one embodiment, a microarray comprises polynucleotide probes that hybridize to the specified miRNA, on a substrate. In another embodiment, a microarray comprises multiple primers or antibodies, optionally immobilized on a substrate.

A change in expression of an miRNA required for diagnosis or detection by the methods described herein refers to an miRNA whose expression is activated to a higher or lower level in a subject having a condition or suffering from a disease, specifically lung cancer or NSCLC, relative to its expression in a reference subject or reference standard. miRNAs may also be expressed to a higher or lower level at different stages of the same disease or condition. Expression of specific miRNAs differ between normal subjects who never smoked or are current or former smokers, and subjects suffering from a disease, specifically COPD, benign lung nodules, or cancer, or between various stages of the same disease. Expression of specific miRNAs differ between pre-surgery and post-surgery patients with lung cancer. Such differences in miRNA expression include both quantitative, as well as qualitative, differences in the temporal or cellular expression patterns among, for example, normal and diseased cells, or among cells which have undergone different disease events or disease stages. For the purpose of this invention, a significant change in miRNA expression when compared to a reference standard is considered to be present when there is a statistically significant ($p<0.05$) difference in miRNA expression between the subject and reference standard or profile.

In the context of the compositions and methods described herein, reference to "at least two," "at least five," etc. of the miRNAs listed in any particular miRNA set means any and all combinations of the miRNAs identified. Specific miRNAs for the miRNA profile do not have to be in rank order in Table 1 and may be any miRNA identified herein.

One skilled in the art may readily reproduce the compositions and methods described herein by use of the sequences of the miRNAs, all of which are publicly available from conventional sources, such as MiRBase or ABI, and are reproduced in Table 1 and in the Sequence Listing.

It should be understood that while various embodiments in the specification are presented using "comprising" language, under various circumstances, a related embodiment is also be described using "consisting of" or "consisting essentially of" language. It is to be noted that the term "a" or "an", refers to one or more, for example, "an miRNA," is understood to represent one or more miRNAs. As such, the terms "a" (or "an"), "one or more," and "at least one" are used interchangeably herein.

Unless defined otherwise in this specification, technical and scientific terms used herein have the same meaning as commonly understood by one of ordinary skill in the art to which this invention belongs and by reference to published texts, which provide one skilled in the art with a general guide to many of the terms used in the present application.

II. miRNA Expression and Expression Profiles

The inventors identified diagnostic miRNA biomarkers and expression profiles consisting of multiple miRNA biomarkers in the peripheral blood lymphocytes of lung cancer (NSCLC) and COPD patients, as well as in populations of healthy smokers and never smokers, and in pre and post-surgical patients. The inventors have discovered that various miRNA expression levels and expression profiles of multiple miRNAs from the PBMCs of lung cancer patients differ significantly from those seen in other populations having non-cancer lung disease or no disease. Changes in the miRNA expression levels or profiles are observed in the normal circulating PBMC of subjects with early stage solid tumors (adenocarcinoma or squamous cell carcinoma), more readily than can be detected in circulating tumor cells, which are present in only vanishing small numbers in early stage lung cancers.

As detailed in the examples below, the inventors have discovered the identity of certain miRNA sequences that can serve either as individual biomarkers to identify an NSCLC from either non-cancerous COPD, or from otherwise healthy populations of current and former smokers, who may have some characteristics of disease due to the smoking history, as well as from populations of never smokers. It is anticipated that some of the miRNA may serve as biomarkers in diagnostic assays in conjunction with one or more additional miRNA biomarkers, so as to form a characteristic signature that can distinguish among the various diseased and healthy populations.

Table 1 identifies the miRNA useful in the methods described herein by miRBase Accession number, by RNA sequence, by ABI Accession number and by name.

TABLE 1

| Sequence | miRBase Acc No. | App. Bio. Part No. | Symbol | SEQ ID NO |
|---|---|---|---|---|
| CAUAAAGUAGAAAGCACUAC | MI0000458/ MIMAT0000433 | 4373135 | miR-142-5p | 1 |
| CUGGCCCUCUCUGCCCUUCCGU | MI0000804/ MIMAT0000752 | 4373049 | miR-328 | 2 |
| UCGGAUCCGUCUGAGCUUGGCU | MI0000472/ MIMAT0000446 | 4373147 | miR-127 | 3 |
| AGCUACAUUGUCUGCUGGGUUUC | MI0000298/ MIMAT0000278 | 4373077 | miR-221 | 4 |
| UCAGUGCAUCACAGAACUUUGU | MI0000811/ MIMAT0000759 | 4373129 | miR-148b | 5 |
| UCAGUGCACUACAGAACUUUGU | MI0000253/ MIMAT0000243 | 4373130 | miR-148a | 6 |
| ACUAGACUGAAGCUCCUUGAGG | MI0000809/ MIMAT0000757 | 4373179 | miR-151 | 7 |
| AGCAGCAUUGUACAGGGCUAUGA | MI0000108/ MIMAT0007402 | 4373158 | miR-103 | 8 |
| UCAAGAGCAAUAACGAAAAAUGU | MI0000816/ MIMAT0000765 | 4373045 | miR-335 | 9 |
| UCGUACCGUGAGUAAUAAUGC | MI0000471/ MIMAT0000445 | 4378064 | miR-126 | 10 |
| UAAGGUGCAUCUAGUGCAGAUA | MI0000072/ MIMAT0000072 | 4373118 | miR-18a | 11 |
| AGAGGUAGUAGGUUGCAUAGU | MI0000065/ MIMAT0000065 | 4373166 | let-7d | 12 |
| CAAAGAAUUCUCCUUUUGGGCUU | MI0000483 | 4373112 | miR-186 | 13 |
| AAUGACACGAUCACUCCCGUUGA | MI0001448/ MIMAT0003393 | 4380926 | miR-425-5p | 14 |
| GCCCCUGGGCCUAUCCUAGAA | MI0000812/ MIMAT0000760 | 4373046 | miR-331 | 15 |
| CAAAGUGCUUACAGUGCAGGUAGU | | 4373119 | miR-17-5p | 16 |
| UAGCAGCACAUCAUGGUUUACA | MI0000438/ MIMAT0000417 | 4373122 | miR-15b | 17 |
| UGAGGUAGUAGGUUGUAUAGUU | MIMAT0000062 | 4373169 | let-7a | 18 |
| AAACCGUUACCAUUACUGAGUUU | MI0001729 | 4373209 | miR-451 | 19 |
| GGCAAGAUGCUGGCAUAGCUG | MI0000089 | 4373190 | miR-31 | 20 |
| UCCUGUACUGAGCUGCCCCGAG | MI0002470 | 4378096 | miR-486 | 21 |

TABLE 1-continued

| Sequence | miRBase Acc No. | App. Bio. Part No. | Symbol | SEQ ID NO |
|---|---|---|---|---|
| CAAAGUGCUCAUAGUGCAGGUAG | MI0001519/ MIMAT0001413 | 4373263 | miR-20b | 22 |
| CUUUCAGUCGGAUGUUUACAGC | MIMAT0000693 | 4373057 | miR-30e-3p | 23 |
| AGCUCGGUCUGAGGCCCCUCAG | MI0001445/ MIMAT0001340 | 4373015 | miR-423 | 24 |
| UACAGUAGUCUGCACAUUGGUU | | 4378068 | miR-199a | 25 |
| AAAGUGCUGUUCGUGCAGGUAG | MI0000095 | 4373012 | miR-93 | 26 |
| AAGGAGCUCACAGUCUAUUGAG | MI0000086/ MIMAT0000085 | 4373067 | miR-28 | 27 |
| UAGCUUAUCAGACUGAUGUUGA | MI0000077/ MIMAT0000076 | 4373090 | miR-21 | 28 |
| AGCUACAUCUGGCUACUGGGUCUC | MI0000299 | 4373076 | miR-222 | 29 |
| UGUAAACAUCCUUGACUGGA | MIMAT0000692 | 4373058 | miR-30e-5p | 30 |
| CCCAUCUGGGGUGGCCUGUGACUUU | | 4380958 | miR-594 | 31 |
| UCCGUCUCAGUUACUUUAUAGCC | MI0000802 | 4373041 | miR-340 | 32 |
| CAUUAUUACUUUUGGUACGCG | MI0000471 | 4373269 | miR-126 | 33 |
| CAGUGCAAUGUUAAAAGGGCAU | MI0000448/ MIMAT0000425 | 4373145 | miR-130a | 34 |
| CAUUGCACUUGUCUCGGUCUGA | MI0000082/ MIMAT0000081 | 4373071 | miR-25 | 35 |
| UACCCAUUGCAUAUCGGAGUUG | MI0003684/ MIMAT0003338 | 4380925 | miR-660 | 36 |
| AACAUUCAUUGUUGUCGGUGGGUU | MI0003139/ MIMAT0002821 | 4373180 | miR-181d | 37 |
| UCCCUGAGACCCUUUAACCUGUG | MI0000469/ MIMAT0000443 | 4373149 | miR-125a | 38 |
| UUCACAGUGGCUAAGUUCUGC | MI0000440/ MIMAT0000419 | 4373068 | miR-27b | 39 |
| CAUGCCUUGAGUGUAGGACCGU | MI0003205/ MIMAT0002888 | 4380928 | miR-532 | 40 |
| UGGCUCAGUUCAGCAGGAACAG | MIMAT0000080 | 4373072 | miR-24 | 41 |
| AACAUUCAUUGCUGUCGGUGGG | MIMAT0000257 | 4373116 | miR-181b | 42 |
| AAGCUGCCAGUUGAAGAACUGU | MI0000078/ MIMAT0000077 | 4373079 | miR-22 | 43 |
| UGAGGUAGUAGGUUGUAUGGUU | MIMAT0000064 | | miR-let-7c | 44 |
| UGGCAGUGUCUUAGCUGGUUGU | MIMAT0000255 | | miR-34a | 45 |

TABLE 1-continued

| Sequence | miRBase Acc No. | App. Bio. Part No. | Symbol | SEQ ID NO |
|---|---|---|---|---|
| UUCCUAUGCAUAUACUUCUUUG | MIMAT0002810 | | miR-202* | 46 |
| UGAGACCUCUGGGUUCUGAGCU | MIMAT0003886 | | miR-769-5p | 47 |
| GUCCCUCUCCAAAUGUGUCUUG | MIMAT0003312 | | miR-642 | 48 |

Table 1 and FIG. 3 provide a list of identified miRNA biomarkers, and identify them by their conventional miRNA names, as well as by their Accession Nos. in the miRBase and ABI databases. The expression of each miRNA for each of five subject populations is provided using an arbitrary expression number obtained from hierarchical clustering data. In one embodiment of the diagnostic methods described herein, at least a 1.2 fold difference between the miRNA expression levels of two populations is considered significant for purposes of distinguishing between the populations. In another embodiment of the diagnostic methods described herein, at least a 1.5 fold difference between the miRNA expression levels of two populations is considered significant for purposes of distinguishing between the populations. In another embodiment of the diagnostic methods described herein, at least a 1.7 fold difference between the miRNA expression levels of two populations is considered significant for purposes of distinguishing between the populations. In still another embodiment of the diagnostic methods described herein, a >2 fold difference between the miRNA expression levels of two populations is considered significant for purposes of distinguishing between the populations.

In one embodiment, the following miRNA biomarkers are particularly useful alone or in combinations forming a profile for distinguishing between subjects with COPD and subjects with any NSCLC: miR-142-5p, miR-328, miR-127, miR-221, miR-148b, miR-148a, miR-151, miR-103, miR-18a, miR-let-7d, miR-186, miR-15b, miR-let-7a, miR-451, miR-20b, miR-30e-3p, and miR-27b.

In another embodiment, the following miRNA biomarkers are particularly useful alone or in combination forming a profile for distinguishing between subjects with adenocarcinoma vs. squamous cell carcinoma: miR-142-5p, miR-328, miR-148b, miR-151, miR-335, miR-221, miR-126, miR-425-5p, miR-331, miR-31, miR-486, miR-199a and miR-222.

In still another embodiment certain miRNA biomarkers are particularly useful alone or in combinations forming a profile for distinguishing between subjects with COPD and SCC, such as miR-142-5p, miR-328, miR-127, miR-221, miR-148b, miR-148a, miR-151, miR-103, miR-335, miR-126, miR-18a, miR-let-7d, miR-186, miR-425-5p, miR-331, miR-17-5p, as well as others characterized as max ratio COPD/SCC in FIG. 3.

In another embodiment, miR-142-5p and miR-486 are useful biomarkers for distinguishing between healthy smokers and subjects with adenocarcinoma.

In another embodiment, miR-328, miR-221, miR-148b, miR-151, miR-let-7d and miR181d are useful biomarkers for distinguishing between healthy smokers and subjects with squamous cell carcinoma.

In another embodiment, one or more of the miRNAs: hsa-miR-let-7c, hsa-miR-34a, hsa-miR-202, hsa-miR-769-5p, and hsa-miR-642 are useful in distinguishing between lung cancer patients pre-surgery and patients who have had surgery to remove the lung tumors. These biomarkers are useful to monitor the post-surgery progress of this class of subjects.

Similar biomarkers may be selected by calculation of the ratios of expression between selected populations from the arbitrary units provided in FIG. 3 so as to identify expression of miRNA in this groups that are particularly useful alone, or in combinations in profiles to distinguish between, e.g., subjects who are relatively healthy but may have benign lesions due to smoking (S) and subjects with NSCLC in general, or a particularly cancer, such as AC or SCC. Still other miRNA biomarkers are useful alone or in a profile with other biomarkers to distinguish between subjects with lung disease, e.g., COPD but not cancer NSCLC, etc.

It should be understood that based upon the teachings herein the miRNA expression signatures or profiles identified herein for use in identifying any one of the conditions discussed, e.g., an NSCLC or COPD, may be further adjusted to reduce the numbers of miRNA sequences necessary to increase accuracy of diagnosis. Such diagnostic methods and profiles may also be used in conjunction with other known methods of diagnosing or detecting NSCLC and COPD, or any other condition discussed herein to further increase accuracy of diagnosis.

III. Methods of Detecting/Quantifying miRNA

Methods that may be employed in obtaining, detecting and quantifying miRNA expression are known and may be used to accomplish the diagnostic goals of the present invention. See, for example, the techniques described in the examples below, as well as in e.g., WO2008/073923; US Published Patent Application No. 2006/0134639, and U.S. Pat. No. 6,040,138, among others.

For example, the biological samples may be collected using the proprietary PaxGene Blood RNA System (Pre-AnalytiX, a Qiagen, BD company). The PAXgene Blood RNA System comprises two integrated components: PAXgene Blood RNA Tube and the PAXgene Blood RNA Kit. Blood samples are drawn directly into PAXgene Blood RNA Tubes via standard phlebotomy technique. These tubes contain a proprietary reagent that immediately stabilizes intracellular RNA, minimizing the ex-vivo degradation or up-regulation of RNA transcripts. The ability to eliminate freezing, batch samples, and to minimize the urgency to process samples following collection, greatly enhances lab efficiency and reduces costs.

Thereafter, the miRNA are detected and/or measured using a variety of assays. The most sensitive and most flexible quantitative method is real-time polymerase chain reaction (RT-PCR), which can be used to compare miRNA levels in different sample populations, in normal and tumor tissues, with or without drug treatment, to characterize patterns of miRNA expression, to discriminate between closely related miRNAs, and to analyze RNA structure. This method can be employed by using conventional RT-PCR assay kits according to manufacturers' instructions, such as TaqMan® RT-PCR (Applied Biosystems).

The first step is the isolation of RNA from a target sample (e.g., typically total RNA isolated from human PBMC in this case). RNA can be extracted, for example, from frozen or archived paraffin-embedded and fixed (e.g., formalin-fixed) tissue samples. General methods for mRNA extraction are well known in the art, e.g., in standard textbooks of molecular biology, including methods for RNA extraction from paraffin embedded tissues. In particular, RNA isolation can be performed using a purification kit, buffer set and protease from commercial manufacturers, according to the manufacturer's instructions. Exemplary commercial products include TRI-REAGENT, Siegen RNeasy mini-columns, MASTERPURE Complete DNA and RNA Purification Kit (EPICENTRE®, Madison, Wis.), Paraffin Block RNA Isolation Kit (Ambion, Inc.) and RNA Stat-60 (Tel-Test). Conventional techniques such as cesium chloride density gradient centrifugation may also be employed.

Next, in the reverse transcription step, cDNA is reverse transcribed from mRNA samples using primers specific for the miRNAs to be detected. Methods for reverse transcription are well known in the art, e.g., in standard textbooks of molecular biology. Briefly, RNA is first incubated with a primer at 70° C. to denature RNA secondary structure and then quickly chilled on ice to let the primer anneal to the RNA. Other components are added to the reaction including dNTPs, RNase inhibitor, reverse transcriptase and reverse transcription buffer. The reverse transcription reaction is extended at 42° C. for 1 hr. The reaction is then heated at 70° C. to inactivate the enzyme. Optionally, the template RNA may be removed by treating the reverse transcription reaction with RNase H before using the reaction in the real time PCR reaction.

In the RT-PCR step, PCR products are amplified from the cDNA samples. PCR product accumulation is measured through a dual-labeled fluorigenic probe (i.e., TAQMAN® probe). Real time PCR is compatible both with quantitative competitive PCR, where an internal competitor for each target sequence is used for normalization, and with quantitative comparative PCR using a normalization miRNA contained within the sample, or a housekeeping miRNA for RT-PCR. For further details see, e.g. Held et al., Genome Research 6:986 994 (1996).

TaqMan® RT-PCR can be performed using commercially available equipment. In a preferred embodiment, the 5' nuclease procedure is run on a real-time quantitative RCR device such as the ABI PRISM 7900® Sequence Detection System®. The system amplifies samples in a 96 (or 384)-well format on a thermocycler. During amplification, laser-induced fluorescent signal is collected in real-time through fiber optic cables for all 96 (or 384) wells, and detected at the CCD. The system includes software for running the instrument and for analyzing the data. 5'-Nuclease assay data are initially expressed as Ct, or the threshold cycle. As discussed above, fluorescence values are recorded during every cycle and represent the amount of product amplified to that point in the amplification reaction. The point when fluorescent signal is first recorded as statistically significant is the threshold cycle (Ct).

To minimize errors and the effect of sample-to-sample variation, RT-PCR is usually performed using an internal standard. The ideal internal standard is expressed as a constant level among different tissues, and is unaffected by the experimental treatment. RNAs most frequently used to normalize patterns of miRNA expression are mRNAs for the housekeeping miRNAs glyceraldehydes-3phospate-dehydrogenase (GAPDH) and β-actin.

The steps of a representative protocol from profiling miRNA expression using fixed, paraffin-embedded tissues as the RNA source, including mRNA isolation, purification, primer extension and amplification are known to those of skill in the art. Briefly, a representative process starts with cutting about 10 µm thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using miRNA specific promoters followed by RT-PCR.

The specific techniques identified in Example 1 below demonstrate the state of the art. However, other conventional methods of miRNA isolation, detection and quantification can be employed in these methods.

Still other methods of detecting and/or measuring miRNA may be employed, using antibodies or fragments thereof. As used herein, the term "antibody" refers to an intact immunoglobulin having two light and two heavy chains or any fragments thereof. Thus a single isolated antibody or fragment may be a polyclonal antibody, a high affinity polyclonal antibody, a monoclonal antibody, a synthetic antibody, a recombinant antibody, a chimeric antibody, a humanized antibody, or a human antibody. The term "antibody fragment" refers to less than an intact antibody structure, including, without limitation, an isolated single antibody chain, a single chain Fv construct, a Fab construct, a light chain variable or complementarity determining region (CDR) sequence, etc. A recombinant molecule bearing a sequence that binds to the miRNA may also be used in these methods. It should be understood that any antibody, antibody fragment, or mixture thereof that binds a specified miRNA as defined herein may be employed in the methods of the present invention, regardless of how the antibody or mixture of antibodies was generated.

Similarly, methods using genomic or other hybridization probes to identify the miRNA sequences are useful herein. In another embodiment, a suitable assay detection assay is an immunohistochemical assay, a hybridization assay, a counter immuno-electrophoresis, a radioimmunoassay, radioimmunoprecipitation assay, a dot blot assay, an inhibition of competition assay, or a sandwich assay.

Any of the methods described above or otherwise herein may be performed by a computer processor or computer-programmed instrument that generates numerical or graphical data useful in the diagnosis or detection of the condition or differentiation between two conditions.

IV. Compositions of the Invention

The methods for diagnosing or detecting lung disease utilizing defined miRNA biomarker expression levels or profiles of multiple miRNA biomarkers permits the development of simplified diagnostic tools for diagnosing or detecting lung cancer, e.g., NSCLC or diagnosing or detecting a specific stage (early, stage I, stage II or late stage) of lung cancer, diagnosing or detecting a specific type of lung cancer (e.g., AC vs. SCC), distinguishing between COPD and lung cancer or benign lung nodules and lung cancer, and/or monitoring the effect of therapeutic or surgical intervention for determination of further treatment or evaluation of the likelihood of recurrence of the cancer.

In one aspect, diagnostic reagent is capable of specifically complexing with or identifying an miRNA of Table 1. In another embodiment, the reagent comprises a ligand capable of complexing with, hybridizing to, or identifying an miRNA of Table 1. In another embodiment, the miRNA include hsa-miR-148a, hsa-miR-142-5p, hsa-miR-221, hsa-miR-let-7d, hsa-miR-let-7a, hsa-miR-328, hsa-miR-let-7c, hsa-miR-34a, hsa-miR-202, hsa-miR-769-5p, hsa-miR-642, and a combination of two or more thereof. The reagent, in one embodiment, is an amplification nucleic acid primer (such as an RNA primer) or primer pair that amplifies and detects a nucleic acid sequence of said miRNA. In another embodiment, the reagent is a polynucleotide probe that hybridizes to the miRNA nucleic acid sequence. In another embodiment, the reagent is an antibody or fragment of an antibody. The reagent can include multiple said primers, probes or antibodies, each specific for at least one miRNA of Table 1. In certain embodiments, the reagent is immobilized on a substrate. Exemplary substrates include a microarray, chip, microfluidics card, or chamber.

Optionally, the diagnostic reagent can be associated with a conventional detectable label. As used herein, "labels" or "reporter molecules" are chemical or biochemical moieties useful for labeling a nucleic acid (including a single nucleotide), polynucleotide, oligonucleotide, or protein ligand, eg, amino acid or antibody. "Labels" and "reporter molecules" include fluorescent agents, chemiluminescent agents, chromogenic agents, quenching agents, radionucleotides, enzymes, substrates, cofactors, inhibitors, magnetic particles, and other moieties known in the art. "Labels" or "reporter molecules" are capable of generating a measurable signal and may be covalently or noncovalently joined to an oligonucleotide or nucleotide (eg, a non-natural nucleotide) or ligand.

A kit or microarray useful in the methods described herein can include at least two such diagnostic reagents, each reagent specific for a different miRNA of Table 1 or FIG. 3. In still another embodiment, a kit or microarray includes at least 3, at least 4, at least 5, at least 6, at least 7, 8, 9, 10, 11, 12, 13, 14, 15, 16, 17, 18 19, at least 20, at least 25 or more such diagnostic reagents, each reagent specific for a different miRNA. One of skill in the art will recognize that all integers occurring between the numbers specified above are included in this disclosure, even if not specifically recited herein.

In another aspect, a composition for diagnosing or detecting lung cancer in a mammalian subject includes at least two PCR primers or probes. Each primer or probe amplifies a different polynucleotide sequence from a miRNA expression product of at least two miRNAs from TABLE 1 found in the peripheral blood mononuclear cells (PBMC) of the subject. These miRNAs are selected to form a miRNA expression profile or signature which is distinguishable between a subject having lung cancer and a selected reference population or standard. Changes in expression in the individual miRNAs or miRNA expression profile of a tested subject from that of a reference miRNA expression profile are correlated with a lung disease, such as non-small cell lung cancer (NSCLC).

In one embodiment of this composition, the primers are those that target miRNAs selected from among the miRNAs identified in TABLE 1. This collection of miRNAs includes those for which expression is altered (i.e., increased or decreased) versus the same miRNA biomarker expression in the PBMC of a reference. In one embodiment, PCR primers and probes are provided to detect at least two miRNAs from TABLE 1 for use in the composition. In another embodiment, PCR primers and probes are provided to detect at least 3, 4, 5, 6, 7, 8, 9, 10, 11, 12, 13, 14, 15, 16, 17, 18, 19, or 20 miRNAs from TABLE 1 for use in the composition. In still another embodiment, PCR primers and probes are provided more than 20, but less than 43 miRNAs from TABLE 1 for use in the composition. The primers or probes used to target the selected miRNAs from the TABLE 1 and FIG. 3 need not be in rank order; rather any combination that clearly targets miRNAs that show a difference in expression between the reference population to the diseased population is useful in such a composition.

In one embodiment, the composition contains primers or probes useful to identify at least two of the following miRNAs: hsa-miR-148a, hsa-miR-142-5p, hsa-miR-221, hsa-miR-let-7d, hsa-miR-let-7a and hsa-miR-328. In another exemplary embodiment, the composition contains primers useful to identify at least two or more of the following miRNAs: miR-142-5p, miR-328, miR-127, miR-221, miR-148b, miR-148a, miR-151, miR-103, miR-18a, miR-let-7d, miR-186, miR-15b, miR-let-7a, miR-451, miR-20b, miR-30e-3p, and miR-27b. In another exemplary embodiment, the composition contains primers useful to identify at least two or more of the following miRNAs: miR-142-5p, miR-328, miR-148b, miR-151, miR-335, miR-221, miR-126, miR-425-5p, miR-331, miR-31, miR-486, miR-199a and miR-222. In another exemplary embodiment, the composition contains primers useful to identify at least two or more of the following miRNAs: miR-142-5p, miR-328, miR-127, miR-221, miR-148b, miR-148a, miR-151, miR-103, miR-335, miR-126, miR-18a, miR-let-7d, miR-186, miR-425-5p, miR-331, miR-17-5p. In another exemplary embodiment, the composition contains primers useful to identify at least two or more of the following miRNAs: miR-142-5p and miR-486. In another exemplary embodiment, the composition contains primers useful to identify at least two or more of the following miRNAs: miR-328, miR-221, miR-148b, miR-151, miR-let-7d and miR181d. In another embodiment, the composition contains primers used to identify two or more of hsa-miR-let-7a, hsa-miR-328, hsa-miR-let-7c, hsa-miR-34a, hsa-miR-202, hsa-miR-769-5p, hsa-miR-642. As discussed above, other specific compositions containing various combinations of the miRNA disclosed in TABLE 1 are encompassed.

As provided above, the reference may be any population class as described above in "Definitions".

The composition, which can be presented in the format of a microfluidics card, a chip or chamber preferably employs the RT-PCR techniques described above. In one aspect, such a format is a diagnostic assay using TAQMAN® Quantitative PCR low density arrays. Preliminary results suggest the number of miRNAs required is compatible with these platforms. When a sample of PBMC from a selected patent subject is contacted with the primers and probes in the composition, PCR amplification of targeted miRNAs in the miRNA expression profile from the patient occurs. The composition thus permits detection of changes in expression in the miRNAs in the miRNA expression profile from that of a reference miRNA expression standard or profile. Significant changes in the miRNA expression of the one or more miRNA biomarkers in the patient's PBMC from that of the reference correlate with a diagnosis of non-small cell lung cancer (NSCLC), a stage of such cancer, a type of such cancer, or a non-cancerous condition, such as COPD, benign lung lesions or nodules, or none of these conditions.

For use in the above-noted compositions the PCR primers and probes are preferably designed based upon the miRNA sequences or their complement(s) identified in TABLE 1. The design of the primer and probe sequences is within the skill of the art once the particular miRNA target is selected. The particular methods selected for the primer and probe design and the particular primer and probe sequences are not limiting features of these compositions. A ready explanation of primer and probe design techniques available to those of skill in the art by resort to general texts as well as commercial manufacturers (e.g., Applied Biosystems).

In one embodiment, optimal PCR primers and probes used in the compositions described herein are about 12-22 bases in length, and contain about 20-80%, such as, for example, about 50-60% G+C bases. Melting temperatures of between 50 and 80° C., e.g. about 50 to 70° C. are typically preferred.

These compositions may be used to diagnose NSCLC lung cancer of stage I or stage II NSCLC. Further these compositions are useful to provide a supplemental or original diagnosis in a subject having lung nodules of unknown etiology.

V. Diagnostic Methods

All of the above-described compositions provide a variety of diagnostic tools which permit a blood-based, non-invasive assessment of disease status in a subject. Use of these compositions in diagnostic tests, which may be coupled with other screening tests, such as a chest X-ray or CT scan, increase diagnostic accuracy and/or direct additional testing. In other aspects, the diagnostic compositions and tools described herein permit the prognosis of disease, monitoring response to specific therapies, and regular assessment of the risk of recurrence. The methods and use of the compositions described herein also permit the evaluation of changes in diagnostic miRNA levels or profiles pre-therapy, pre-surgery and/or at various periods during therapy and post therapy samples and identifies a miRNA expression profile or signature that may be used to assess the probability of recurrence.

In one embodiment, a method of diagnosing or detecting or assessing a condition in a mammalian subject comprises detecting in a biological sample of the subject, or from an miRNA expression profile generated from the sample, the expression level of an miRNA nucleic acid sequence identified in Table 1; and comparing the miRNA expression level or miRNA expression profile in the subject's sample to a reference miRNA standard. A change in expression of the subject's sample miRNA from that in the reference miRNA standard indicates a diagnosis or prognosis of a condition mentioned above. In certain embodiments, the condition is a lung cancer, chronic obstructive pulmonary disease (COPD), or benign lung nodules. These methods may be employed using the biological samples discussed above. In certain embodiments, the biological sample is whole blood, peripheral blood mononuclear cells, plasma and serum.

As discussed above, this method involves in certain embodiments, measuring the expression level of one or more specified miRNA in the subject's sample. In other embodiments, the detecting, measuring or comparing steps of the method are repeated multiple times. For example, in certain embodiments, the miRNA levels are detected or measured in a series of samples of said subject taken at different times. This permits identification of a pattern of altered expression of said miRNA from a selected reference miRNA standard.

In still other embodiments, the detecting or measuring step involves contacting a biological sample from the subject with a diagnostic reagent, such as those described above that identifies or measures the miRNA expression level in the sample. In certain embodiments, the contacting step involves or comprises forming a direct or indirect complex in said biological samples between a diagnostic reagent for said miRNA and the miRNA in the sample. Thereafter, the method measures a level of the complex in a suitable assay, such as described herein.

In one embodiment, the method involves diagnosing or detecting the one or more, or a pattern made up of one or more, of the miRNA nucleic acid sequences: hsa-miR-148a, hsa-miR-142-5p, hsa-miR-221, hsa-miR-let-7d, hsa-miR-let-7a, hsa-miR-328, hsa-miR-let-7c, hsa-miR-34a, hsa-miR-202, hsa-miR-769-5p, hsa-miR-642, and a combination of two or more thereof.

In certain embodiments of these methods, the miRNA(s) is differentially expressed in two or more of the conditions selected from no lung disease with no history of smoking, no lung disease with a history of smoking, lung cancer, chronic obstructive pulmonary disease (COPD), benign lung nodules, lung cancer prior to tumor resection, and lung cancer following tumor resection.

Depending on the conditions being assessed by the methods, the reference miRNA standard is obtained from a reference subject or reference population such as (a) a reference human subject or population having a non-small cell lung cancer (NSCLC); (b) a reference human subject or population having COPD, (c) a reference human subject or population who are healthy and have never smoked, (d) a reference human subject or population who are former smokers or current smokers with no disease; (e) a reference human subject or population having benign lung nodules; (f) a reference human subject or population following surgical removal of an NSCLC tumor; (g) a reference human subjects or population prior to surgical removal of an NSCLC tumor; and (h) the same subject who provided a temporally earlier biological sample.

Thus, in one aspect, a method is provided for diagnosing or detecting a lung disease in a mammalian subject comprising detecting in a human subject's sample, e.g., peripheral blood mononuclear cells (PBMC) or whole blood, or from an miRNA expression profile generated from the sample, the expression level of at least one of the miRNA nucleic acid sequences identified in Table 1 or FIG. 3; comparing the miRNA expression level or profile in the sample to an average expression level or standard of the same miRNA in a reference sample or profile. A change in expression (e.g., increased expression or decreased expression, depending upon the disease and miRNA biomarker involved) of at least one the miRNA from that in the reference is indicative of a non small cell lung cancer (NSCLC) or chronic obstructive pulmonary disease (COPD). This method may also be employed to identify a type or stage of NSCLC, as well as enable diagnosis of the absence of malignancy. This method may be performed using the appropriately selected compositions described above.

In another embodiment, a method is provided for diagnosing or detecting a lung disease in a mammalian subject comprising detecting in a sample of the subject's peripheral blood mononuclear cells (PBMC) or whole blood, or from an miRNA expression profile generated from the sample, the expression level of at least one of the miRNA nucleic acid sequences selected from the group consisting of hsa-miR-148a, hsa-miR-142-5p, hsa-miR-221, hsa-miR-let-7d, hsamiR-let-7a and hsa-miR-328; and comparing the miRNA expression level in the sample to an average expression level or standard of the same miRNA in a reference sample or profile. A change in expression of at least one the miRNA from that in the reference is indicative of a non small cell lung cancer (NSCLC) or chronic obstructive pulmonary disease (COPD).

In other embodiments of these methods, the assessment or identification of miRNAs to distinguish or identify a condition may be coupled with the assessment or identification of mRNA sequences or gene sequences or an expression profile of same characteristic of the same condition. For example, the methods described above may further comprise additional steps. For example, the method can employ detecting in the biological sample of the subject, or from a gene expression profile generated from the sample, the expression level of a gene associated with the condition. The gene expression level or gene profile of the subject's sample is then compared to a reference gene standard; and the expression level or profile of the miRNA obtained as above is correlated with the expression level or profile of the gene or mRNA sequences. In such a method, the combined changes in expression of the miRNA and the gene from their levels of expression in the reference miRNA standard and reference gene standard, respectively, indicates a diagnosis or prognosis of the condition. See e.g., International patent publication No. Pub No. WO 2009/075799, among other gene sequences that may be correlated with the miRNAs of these methods to enhance or make a diagnosis or detect a specific condition.

More specific embodiments of these diagnostic methods are described below.

A. Methods of Diagnosing or Detecting NSCLC

Thus, in one embodiment, a method of diagnosing or detecting squamous cell carcinoma in a mammalian subject involves detecting in a sample of the subject's peripheral blood mononuclear cells (PBMC), or from an miRNA expression profile generated from the sample, the expression level of the miRNA nucleic acid sequences hsa-miR-148a. In one embodiment, a method of diagnosing or detecting squamous cell carcinoma in a mammalian subject involves detecting in a sample of the subject's whole blood, or from an miRNA expression profile generated from the sample, the expression level of the miRNA nucleic acid sequences hsa-miR-148a. The miRNA expression level of the specified miRNA in the sample is compared to an average expression level of the same miRNA in a reference sample or profile. Where the reference standard or profile is from one or more subjects with chronic obstructive pulmonary disease (COPD), a decrease in expression of the miRNA from that in the reference is indicative of squamous cell carcinoma. Where the reference standard or profile is from one or more healthy subjects who have never smoked, a decrease in expression of the miRNA from that in the reference is indicative of squamous cell carcinoma. Where the reference standard or profile is from one or more former or current smokers who have no disease, a decrease in expression of the miRNA from that in the reference is indicative of squamous cell carcinoma. Where the reference standard is a standard or profile derived from the PBMC of a reference human subject, or an average of multiple subjects, who have benign lung nodules, a decrease in expression of the miRNA from that in the reference is indicative of squamous cell carcinoma. Where the reference standard or profile is from one or more subjects with early stage adenocarcinoma, a decrease in expression of the miRNA from that in the reference is indicative of squamous cell carcinoma. In monitoring the progress of an SCC patient undergoing treatment, the expression levels of the miRNA may be compared in earlier and later biological samples from the subject. An increase in expression of this miRNA in the later samples may indicate that the therapeutic regimen is effective. The opposite is true with successive decreases in expression.

Thus in the diagnosis of NSCLC from other non-cancerous lung diseases, this miRNA biomarker alone or in combination with other miRNA biomarkers in a profile is useful in diagnostic methods.

In still another aspect, a method of diagnosing or detecting non-small cell lung cancer (NSCLC) in a mammalian subject involves detecting in a sample of the subject's peripheral blood mononuclear cells (PBMC), or from an miRNA expression profile generated from the sample, the expression level of the miRNA nucleic acid sequences hsa-miR-let-7a. In another aspect, a method of diagnosing or detecting non-small cell lung cancer (NSCLC) in a mammalian subject involves detecting in a sample of the subject's whole blood, or from an miRNA expression profile generated from the sample, the expression level of the miRNA nucleic acid sequences hsa-miR-let-7a. The miRNA expression level of the specified miRNA in the sample is compared to an average expression level of the same miRNA in a reference sample or profile. The miRNA expression level of the specified miRNA in the sample is compared to an average expression level of the same miRNA in a reference standard or profile. Where the reference standard or profile is from one or more subjects with chronic obstructive pulmonary disease (COPD), a decrease in expression of the miRNA from that in the reference is indicative of NSCLC. Where the reference standard is a standard or profile derived from the PBMC of a reference human subject, or an average of multiple subjects, who have benign lung nodules, a decrease in expression of the miRNA from that in the reference is indicative of NSCLC. Where the reference standard or profile is from one or more healthy subjects who have never smoked, a decrease in expression of the miRNA from that in the reference is indicative of NSCLC. Where the reference standard or profile is from one or more former or current smokers who have no disease, a decrease in expression of the miRNA from that in the reference indicates a diagnosis of NSCLC, e.g., squamous cell carcinoma or adenocarcinoma. This biomarker may similarly be employed in assessing therapeutic efficacy in multiple samples from the treated subject as described above.

Thus in the diagnosis of NSCLC from other non-cancerous lung diseases, this miRNA biomarker alone or in combination with other miRNA biomarkers such as miR-148a in a profile is useful in diagnostic methods.

In yet a further aspect, a method of diagnosing or detecting squamous cell carcinoma in a mammalian subject is provided, comprising detecting in a subject's sample, e.g., whole blood or peripheral blood mononuclear cells (PBMC), or from an miRNA expression profile generated from the sample, the expression level of the miRNA nucleic acid sequences hsa-miR-let-7d. The miRNA expression level of the specified miRNA in the sample is compared to an average expression level of the same miRNA in a reference sample or profile. Where the reference standard or profile is from one or more subjects with chronic obstructive pulmonary disease (COPD), a decrease in expression of the miRNA from that in the reference is indicative of SCC. Where the reference standard is a standard or profile derived from the PBMC of a reference human subject, or an average of multiple subjects, who have benign lung nodules, a decrease in expression of the miRNA from that in the reference is indicative of SCC. Where the reference standard or profile is from one or more healthy subjects who have never smoked, a decrease in expression of the miRNA from that in the reference is indicative of SCC. Where the reference standard or profile is from one or more former or current smokers who have no disease, a decrease in expression of the miRNA from that in the reference indicates a diagnosis of SCC. This biomarker may similarly be employed in assessing therapeutic efficacy in multiple samples from the treated subject as described above.

In another aspect, a method of diagnosing or detecting squamous cell carcinoma in a mammalian subject is provided, comprising detecting in a subject's sample, e.g., whole blood or peripheral blood mononuclear cells (PBMC), or from an miRNA expression profile generated from the sample, the expression level of the miRNA nucleic acid sequences hsa-miR-221. The miRNA expression level of the specified miRNA in the sample is compared to an average expression level of the same miRNA in a reference sample or profile. Where the reference standard or profile is from one or more subjects with chronic obstructive pulmonary disease (COPD), a decrease in expression of the miRNA from that in the reference is indicative of SCC. Where the reference standard is a standard or profile derived from the PBMC of a reference human subject, or an average of multiple subjects, who have benign lung nodules, a decrease in expression of the miRNA from that in the reference is indicative of SCC. Where the reference standard or profile is from one or more healthy subjects who have never smoked, a decrease in expression of the miRNA from that in the reference is indicative of SCC. Where the reference standard or profile is from one or more former or current smokers who have no disease, a decrease in expression of the miRNA from that in the reference indicates a diagnosis of SCC. This biomarker may similarly be employed in assessing therapeutic efficacy in multiple samples from the treated subjects as described above.

Thus in the diagnosis of SCC from other non-cancerous lung diseases, one or both the miRNA biomarkers miR-let-7d or miR-221 alone or in combination with other miRNA biomarkers in a profile is useful in diagnostic methods.

In another aspect, a method of diagnosing or detecting adenocarcinoma in a mammalian subject is provided, comprising detecting in a biological sample of the subject, e.g., whole blood or peripheral blood mononuclear cells (PBMC), or from an miRNA expression profile generated from the sample, the expression level of the miRNA nucleic acid sequences hsa-miR-142-5p. The miRNA expression level of the specified miRNA in the sample is compared to an average expression level of the same miRNA in a reference sample or profile. Where the reference standard or profile is from one or more subjects with chronic obstructive pulmonary disease (COPD), a decrease in expression of the miRNA from that in the reference is indicative of AC. Where the reference standard is a standard or profile derived from the PBMC of a reference human subject, or an average of multiple subjects, who have benign lung nodules, a decrease in expression of the miRNA from that in the reference is indicative of AC. Where the reference standard or profile is from one or more healthy subjects who have never smoked, a decrease in expression of the miRNA from that in the reference is indicative of AC. Where the reference standard or profile is from one or more former or current smokers who have no disease, a decrease in expression of the miRNA from that in the reference indicates a diagnosis of AC. This biomarker may similarly be employed in assessing therapeutic efficacy in multiple samples from the treated subject as described above.

Thus in the diagnosis of AC from other non-cancerous lung diseases, the miRNA biomarker miR-142-5p alone or in combination with other miRNA biomarkers in a profile is useful in diagnostic methods.

In another aspect, a method of diagnosing or detecting the type of NSCLC in a mammalian subject is provided, comprising detecting in a sample of the subject's peripheral blood mononuclear cells (PBMC), or from an miRNA expression profile generated from the sample, the expression level of the miRNA nucleic acid sequences hsa-miR-148a. The miRNA expression level of the specified miRNA in the sample is compared to an average expression level of the same miRNA in a reference sample or profile. Where the reference standard or profile is from one or more subjects diagnosed with SCC, a decrease in expression of the miRNA from that in the reference is indicative of a diagnosis of adenocarcinoma. Where the reference standard or profile is from one or more subjects diagnosed with AC, an increase in expression of the miRNA from that in the reference is indicative of a diagnosis of SCC. This biomarker may similarly be employed in assessing therapeutic efficacy in multiple samples from the treated subject as described above.

In another aspect, a method of diagnosing or detecting adenocarcinoma in a mammalian subject is provided, comprising detecting in a biological sample of the subject, e.g., whole blood or peripheral blood mononuclear cells (PBMC), or from an miRNA expression profile generated from the sample, the expression level of the miRNA nucleic acid sequences hsa-miR-328. The miRNA expression level of the specified miRNA in the sample is compared to an average expression level of the same miRNA in a reference sample or profile. Where the reference standard or profile is from one or more subjects with the NSCLC, squamous cell carcinoma, wherein an increase in the subject level from the reference level is indicative of a diagnosis of adenocarcinoma. This biomarker may similarly be employed in assessing therapeutic efficacy in multiple samples from the treated subject as described above.

Thus in the diagnosis of AC from other cancerous lung diseases, the miRNA biomarker miR-328 alone or in combination with other miRNA biomarkers in a profile is useful in diagnostic methods.

In another aspect, a method of diagnosing or detecting SCC in a mammalian subject is provided, comprising detecting in a biological sample of the subject, e.g., whole blood or peripheral blood mononuclear cells (PBMC), or from an miRNA expression profile generated from the sample, the expression level of the miRNA nucleic acid sequences hsa-miR-328. The miRNA expression level of the specified miRNA in the sample is compared to an average expression level of the same miRNA in a reference sample or profile. Where the reference standard or profile is from one or more subjects who are healthy and have never smoked, a decrease in the subject level from the reference level is indicative of a diagnosis of SCC. This biomarker may similarly be employed in assessing therapeutic efficacy in multiple samples from the treated subject as described above.

Thus in the diagnosis or detection of SCC, the miRNA biomarker miR-328 alone or in combination with other miRNA biomarkers in a profile is useful in diagnostic methods.

Still other similar methods are contemplated based upon other miRNA identified in Table 1 and for which the fold expression between two populations is useful in distinguishing COPD from NSCLC, in distinguish between the NSCLC stages and types and indistinguishing subjects with benign nodules or other lung lesions related to smoking from a specified lung disease.

B. Methods of Diagnosing or Detecting COPD

In another aspect, a method of diagnosing or detecting chronic obstructive pulmonary disease (COPD) in a mammalian subject involves detecting in a sample of the subject, e.g., whole blood or peripheral blood mononuclear cells (PBMC), or from an miRNA expression profile generated from the sample, the expression level of the miRNA nucleic acid sequences hsa-miR-let-7d. The miRNA expression level of the specified miRNA in the sample is compared to an average expression level of the same miRNA in a reference sample or profile. Where the reference standard is a standard or profile derived from the PBMC of a reference human subject, or an average of multiple subjects, who have benign lung nodules, an increase in expression of the miRNA from that in the reference is indicative of COPD. Where the reference standard or profile is from one or more healthy subjects who have never smoked, an increase in expression of the miRNA from that in the reference is indicative of COPD. Where the reference standard or profile is from one or more former or current smokers who have no disease, an increase in expression of the miRNA from that in the reference indicates a diagnosis of COPD. Where the reference standard or profile is from one or more subjects diagnosed with AC, an increase in expression of the miRNA from that in the reference indicates a diagnosis of COPD. Where the reference standard or profile is from one or more subjects diagnosed with SCC, an increase in expression of the miRNA from that in the reference indicates a diagnosis of COPD. This biomarker may similarly be employed in assessing therapeutic efficacy in multiple samples from the treated subject as described above.

In another aspect, a method of diagnosing or detecting chronic obstructive pulmonary disease (COPD) in a mammalian subject is provided, comprising detecting in a sample, e.g., the subject's whole blood or peripheral blood mononuclear cells (PBMC), or from an miRNA expression profile generated from the sample, the expression level of the miRNA nucleic acid sequences hsa-miR-221. The miRNA expression level of the specified miRNA in the sample is compared to an average expression level of the same miRNA in a reference sample or profile. Where the reference standard is a standard or profile derived from the PBMC of a reference human subject, or an average of multiple subjects, who have benign lung nodules, an increase in expression of the miRNA from that in the reference is indicative of COPD. Where the reference standard or profile is from one or more healthy subjects who have never smoked, an increase in expression of the miRNA from that in the reference is indicative of COPD. Where the reference standard or profile is from one or more former or current smokers who have no disease, an increase in expression of the miRNA from that in the reference indicates a diagnosis of COPD. Where the reference standard or profile is from one or more subjects diagnosed with AC, an increase in expression of the miRNA from that in the reference indicates a diagnosis of COPD. Where the reference standard or profile is from one or more subjects diagnosed with SCC, an increase in expression of the miRNA from that in the reference indicates a diagnosis of COPD. This biomarker may similarly be employed in assessing therapeutic efficacy in multiple samples from the treated subject as described above.

Thus in the diagnosis of COPD from lung cancer, one or both the miRNA biomarkers miR-let-7d or miR-221 alone or in combination with other miRNA biomarkers in a profile is useful in diagnostic methods.

C. Method of Monitoring Post-Surgery Subjects

In another aspect, a method of diagnosing or detecting an NSCLC or recurrence of same, or a method for monitoring the progress of post-surgery patients is provided. The post-surgery patients are those who have had an NSCLC tumor removed from the lungs. Such patients may be monitored for recurrence or remission following surgery by detecting in a sample, e.g., the subject's whole blood or peripheral blood mononuclear cells (PBMC), or from an miRNA expression profile generated from the sample, the expression level of one or more of the miRNA nucleic acid sequences hsa-miR-let-7c, hsa-miR-34a, hsa-miR-202, hsa-miR-769-5p, and hsa-miR-642. The miRNA expression level of the one or more specified miRNA in the sample is compared to an average expression level of the same miRNA in a reference sample or profile. Where the reference standard is a standard or profile derived from the biological sample of the same subject before surgery, or an average of multiple subjects, who have not had surgery for tumor removal, a change in expression of the miRNA between post- and pre-surgery can indicate whether the cancer is recurring or remitting. See, e.g., Example 3. These biomarkers or a pattern thereof may be employed in assessing therapeutic efficacy in multiple samples from the treated subject as described above.

Thus in the monitoring of post-surgery samples from lung cancer subjects, one or both the miRNA biomarkers identified above, in combination with other miRNA biomarkers in a profile is useful to monitor patient progress.

Still other similar methods are contemplated based upon other miRNA identified in Table 1 and for which the fold expression between two populations is useful in distinguishing COPD from NSCLC, in distinguish between the NSCLC stages and types and indistinguishing subjects with benign nodules or other lung lesions related to smoking from a specified lung disease.

The diagnostic compositions and methods described herein provide a variety of advantages over current diagnostic methods. Among such advantages are the following. As exemplified herein, subjects with adenocarcinoma or squamous cell carcinoma of the lung, the two most common types of lung cancer are distinguished from subjects with non-malignant lung diseases including chronic obstructive lung disease (COPD) or granuloma or other benign tumors. These methods and compositions provide a solution to the practical diagnostic problem of whether a patient who presents at a lung clinic with a small nodule has malignant disease. Patients with an intermediate-risk nodule would clearly benefit from a non-invasive test that would move the patient into either a very low-likelihood or a very high-likelihood category of disease risk. An accurate estimate of malignancy based on a miRNA profile (i.e. estimating a given patient has a 90% probability of having cancer versus estimating the patient has only a 5% chance of having cancer) would result in fewer surgeries for benign disease, more early stage tumors removed at a curable stage, fewer follow-up CT scans, and reduction of the significant psychological costs of worrying about a nodule. The economic impact would also likely be significant, such as reducing the current estimated cost of additional health care associated with CT screening for lung cancer, i.e., $116,000 per quality adjusted life-year gained. A non-invasive PBMC miRNA test that has a sufficient sensitivity and specificity would significantly alter the post-test probability of malignancy and thus, the subsequent clinical care.

A desirable advantage of these methods over existing methods is that they are able to characterize the disease state from a minimally-invasive procedure, i.e., by taking a blood sample. They are also able to be performed on subjects having very small tumors in which a biopsy would be problematic or on subjects in whom no tumor is known or visible. Blood samples have an additional advantage, which is that the material is easily prepared and stabilized for later analysis. Thus, the methods and compositions described herein could prevent patients from undergoing unnecessary procedures (i.e. if a small lung nodule is discovered) or potential be used to screen high risk patients. The methods and compositions described herein may also be useful in other populations, i.e., to screen certain high-risk lung cancer populations, such as asbestos exposed smokers. In yet another embodiment, the methods and compositions described herein may be used in conjunction with clinical risk factors to help physicians make more accurate decisions about how to manage patients with lung nodules.

The invention is now described with reference to the following examples. These examples are provided for the purpose of illustration only and the invention should in no way be construed as being limited to these examples but rather should be construed to encompass any and all variations that become evident as a result of the teaching provided herein. As disclosed below in the examples, miRNA expression patterns for the miRNAs; miR148a, miR221, and miR142-5p are discovered to be useful to distinguish early non-small cell lung cancer from an at risk control group of chronic obstructive pulmonary diseases with similar smoking histories. miR-221 was observed to decline in blood of early non-small cell lung cancer patients. The increased miR-221 levels in peripheral blood mononuclear cells of chronic obstructive pulmonary disease patients compared to early non-small cell lung cancer and non-diseased controls likely reflects impaired proliferation and accelerated differentiation of bronchoepithelial cells via kit regulatory cell cycle mechanism, possibly predisposing cells for malignancy. Significantly lower miR-142-5p levels were found in blood of early adenocarcinoma patients compared to diseased (chronic obstructive pulmonary disease) and non-diseased (smoker, never smoker) controls. Let-7d expression was significantly lower in stage SCC patients compared to chronic obstructive pulmonary disease. Interestingly, no difference was found in peripheral blood miR-155 expression between non-small cell lung cancer and chronic obstructive pulmonary disease (data not shown), although it is anticipated to be useful in distinguishing between other populations.

Example 1: Changes in MicroRNA Expression in PBMC Associated with Early Stage NSCLC-Isolation and Taqman® Low Density Array Assays Lung cancer and chronic obstructive pulmonary disease patient blood samples were collected and blood samples from tobacco smokers and never smokers were collected by a phlebotomist. Peripheral blood mononuclear cells were isolated and total RNA prepared as previously described (Nebozhyn M, et al. 2006 Blood; 107(8):3189-96; Kari L, et al. 2003 J. Exp. Med., 197(11):1477-88) using TriReagent (Sigma). RNA quality and quantity were determined by BioAnalyzer 2100 (Agilent Technologies) and NanoDrop (Thermo Fisher), respectively. The lung adenocarcinoma (AC-E) and squamous cell carcinoma (SCC-E) samples were from metastasis free stage I and II non-small cell lung cancer patients. The control groups comprised primarily smokers and ex-smokers diagnosed with chronic obstructive pulmonary disease (COPD), current and past smokers without diagnosed chronic airway inflammation (S) and never smokers (NS).

The ABI TLDA, a quantitative RealTime PCR (qRT-PCR) platform that allows simultaneous detection of 365 mature human miRNAs (ABI catalogue number), was used to assay miRNA expression in RNA pools derived from patient and control groups. Multi-plexed miRNA-specific stem-loop RT primers (ABI) provide the specificity for distinguishing closely related miRNAs from less than 1 ug total RNA without prior small RNA purification making the TLDA platform particularly useful for screening clinical samples. All TaqMan® Low Density Arrays (TLDA) were assayed with RNA pools of 6 individuals to identify candidate differentially expressed miRNAs. The TaqMan® miRNA reverse transcription kit with Human Panel RT primer pool v1.0 (8 pools of 48 miRNA primer sets) was used for cDNA synthesis as directed (ABI). RT reactions were carried out using 50 ng total RNA for each RT primer pool, except where noted (recommended amount 10-100 ng).

TLDA data normalization was carried out using RQ Manager software v1.2. After baseline and threshold adjustments by individual miRNAs in RQ Manager, the data was exported in tab-delimited format and processed further using Matlab 6.5 functions. Ct values were adjusted using the corresponding fluorescence threshold of 0.2 according to the formula: $Ct=RQ\cdot Ct+\log_2(0.2/RQ\cdot Xt)$, where both RQ·Ct (cycle threshold value) and RQ·Xt (fluorescence threshold value) were determined by RQ Manager. In order to avoid switching from one calibrator sample to another while using the delta-delta Ct algorithm, the adjusted Ct values were converted to absolute expression (AE) values according to the formula: $AE=0.2/2^{Ct}$, where 0.2 is ABI's default fluorescence threshold value.

To correct for loading differences, the AE value of each miRNA was normalized to 2 endogenous controls, small nucleolar RNAs (RNU44 and RNU48) previously tested to exhibit consistent expression levels across a large number of different tissues and cell lines Pang Y, et al, 2007 BMC Genomics 8:166). Both controls showed highly correlated expression across our samples (Spearman r=0.96) and the average expression value between RNU44 and RNU48 was used as the normalization coefficient.

TaqMan® Low Density Array data filtering for hierarch clustering was accomplished as follows. Normalized AE data including floored low expression values were filtered to remove miRNAs that did not show fold change (fc) of 2 or more between at least two of the sample pools. Hierarchical clustering was carried out using normalized Euclidean distance for samples and correlation similarity metric for miRNAs. Hierarchical clustering pseudocolor scale represented the log 2-transformed ratio of each miRNA expression value over its average expression across all samples. Matlab 6.5 functions (mostly from Bioinformatics Toolbox) were used for the analysis.

TLDA results were validated with individual TaqMan assays. TaqMan® miRNA reverse transcription kit (Applied Biosystems) was used as follows. Each 15 ul RT reaction contained 100 ng total RNA, 1×RT buffer, 1 mM dNTP mix, 50 U MultiScribe™ reverse transcriptase, 3.76 U RNase inhibitor, and the appropriate 1X Human multiplex RT primer pool (as for TLDA). RT product was then diluted 3-fold for individual TaqMan® miRNA assay. Each 10 μl PCR reaction contained 1.33 μl of diluted RT reaction, 5 μl of 2× TaqMan® Universal PCR mix (Applied Biosystems) and 0.5 μl of 20× individual TaqMan® miRNA assay (Applied Biosystems). The reactions were assembled in 384-well plates in triplicate in the ABI 7900HT, heated at 95° C. for 10 min, followed by 40 cycles of 95° C. for 15 sec and 60° C. for 60 sec. Semi-automated multi-well distribution of samples was done using electronic multi-channel pipettes (Matrix Technologies, Hudson, N.H.). Data was normalized and processed in a same manner as for TLDA. RNU44 and RNU48 controls were run separately and AE values used for normalization of miRNA.

The correlation coefficient (r) between individual TaqMan® assays was calculated using Pearson regression. Comparisons of miRNA expression between individual patient samples (n=9-10 per group) were done using Mann-Whitney U test.

Raw intensities and detection p-values were extracted using Illumina Bead Studio v3.0. Arrays were quantile normalized and average background was subtracted from expression values. Non-informative probes were removed if their intensity was low relative to background in majority of samples or if maximum ratio between any 2 samples was not at least 1.2.

Lists of targets for hsa-let-7a, hsa-let-7d, hsa-miR-142-5p, hsa-miR-148a, hsa-miR-221 and hsa-miR-328 were predicted by miRanda algorithm and retrieved from Memorial Sloan-Kettering Cancer Center database http://www.microrna.org (REF: Betel D, Wilson M, Gabow A, Marks D S, Sander C., The microRNA.org resource: targets and expression. Nucleic Acids Res. 2008 January). Expression levels for genes from each list of predicted targets were correlated with expression levels of corresponding miRNA, using data points from 33 individual samples (10 AC, 11 LSCC, 12 COPD), and only genes with significant negative correlation (p-value<0.05) were retained for further functional analysis. Ingenuity IPA software Core Analysis was performed to find significantly enriched canonical pathways and biological functions for each group of potential direct target candidates.

Results were reported as TLDA performance assessment: reproducibility, fold change detection and input RNA. The technical variability between individual TLDAs and the maximum reliable Ct cut off was empirically assessed as follows: One RNA pool (n=6) was assayed on 3 TLDAs using the same RT product. Two TLDAs were run on the same day and then a $3^{rd}$ TLDA was run one month later to assess RT stability. Data for the three technical replicates were analyzed using Spearman rank correlation (r) on Ct values for individual miRNAs. The average correlation between the replicates was calculated for three possible pair-combinations: run 1 vs. run 2, run 2 vs. run 3, and run 1 vs. run 3.

Figure 1B:
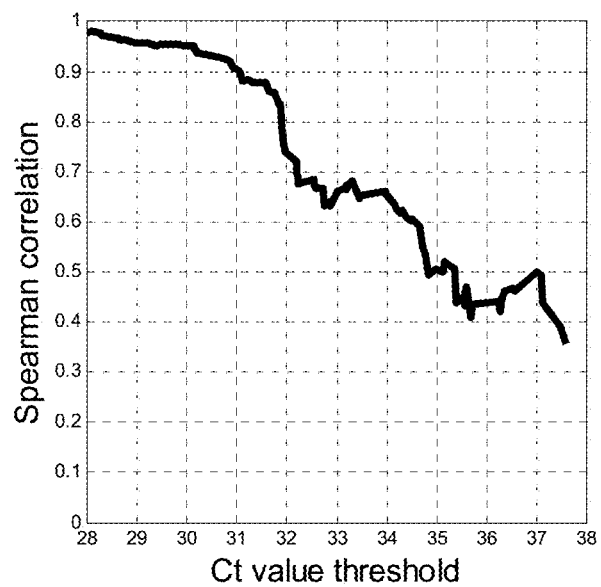
FIG. 1B shows a TLDA reproducibility and sensitivity based on the same correlation analyses of miRNA expression as in FIG. 1A. This graph represents the results of sliding correlation analysis. Calculation of average Spearman correlation is based on expression of 40 miRNAs with Ct values between 28 and 37.5. Ct threshold is the maximum Ct value among 3 replicates.
Figure 2:
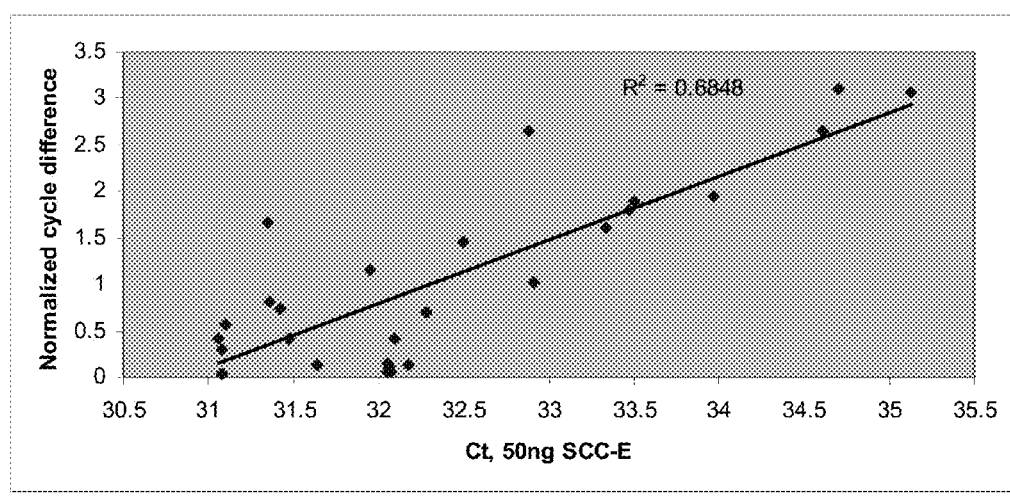
FIG. 2 is a graph showing the effect of higher input RNA on miRNA detectability by TLDA: comparison of 50 and 100 ng of early stage squamous cell carcinoma (SCC) pooled peripheral blood mononuclear cells samples. Each dot represents a newly detected miRNA that was expressed in 50 ng sample at the Ct value listed on X-axis. All graphed miRNAs are expressed below cycle 31 in 100 ng sample. One-half cycle difference is taken as technical error by default. Linear regression analysis shows high correlation of initial Ct values detected in 50 ng sample with normalized cycle difference calculated using both 50 and 100 ng sample data.
Figure 4A:
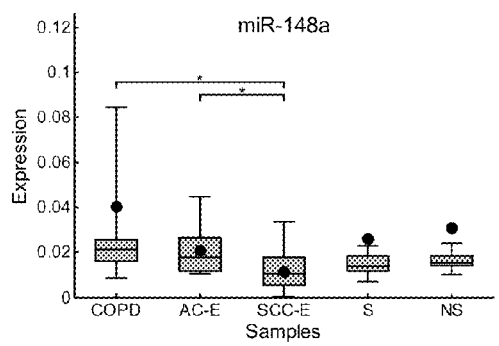
FIG. 4A is an expression profiles for miR-148a of TLDA-derived peripheral blood mononuclear cells miRNAs run on 10 new individual patient samples using single TaqMan® miRNA assays. TLDA-derived normalized expression is represented by (•); COPD represents a population having chronic obstructive pulmonary disease (predominantly former smokers); AC-E represents early stage (stage I+II) adenocarcinoma; SCC-E represents early stage I and II squamous cell carcinoma; S represents smokers without disease; NS represents healthy subjects who have never smoked; (*) represents p<0.05; and (**) represents p<0.01.
Figure 4B:
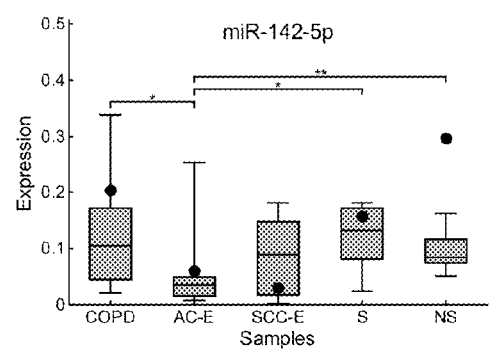
FIG. 4B is an expression profile for miR-142-5p for the samples and using the symbols as defined in FIG. 4A.
Figure 4C:
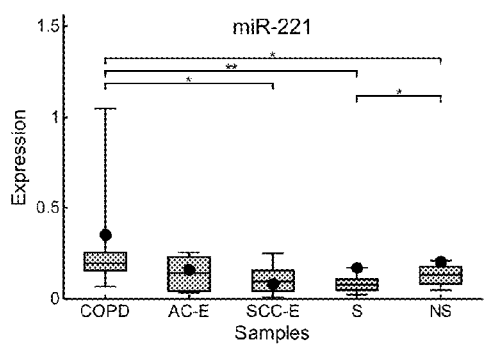
FIG. 4C is an expression profile for miR-221 for the samples and using the symbols as defined in FIG. 4A.
Figure 4D:
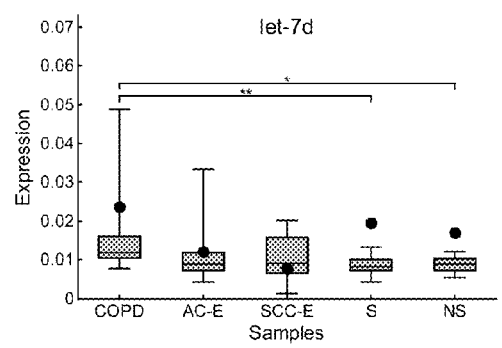
FIG. 4D is an expression profile for miR-let-7d for the samples and using the symbols as defined in FIG. 4A.

Based on Ct values less than 39 the overall correlation between the 3 technical replicates was r=0.98 (FIG. 1A), similar to the correlation between technical replicates using the single TaqMan® assays which was 0.998 for 6 selected miRNAs (data not shown). The high correlation between samples run 1 month apart (run 3) also indicated that the diluted RT product is relatively stable for at least a month when stored at −20° C. The correlations between the 3 replicas begin to decrease between Ct 31-32, indicating the data is less reliable at Ct cutoffs beyond this point. This cutoff is significantly lower then what is usually accepted for single TaqMan® assays. In order to further define the point where reliability decreases, a 'sliding' correlation analysis was used. The sliding window consisting of 40 miRNAs with centered Ct value from 28 to 37.5 was used to calculate average Spearman correlation coefficient between 3 technical replicates based on Ct values for 40 miRNAs. The critical point where the correlations between replicates fell below 0.9 was found to be Ct 31.2. Moreover, at Ct 32 it has dropped to 0.8 (FIG. 1B).

Based on these studies, a Ct value of 31 was used as the upper level cut off for reliable TLDA data. To avoid generating unreliable fold changes for low expressed values, all normalized AE values above the defined Ct cut off of 31, were adjusted to a defined AE value. This flooring level (flooring level) was defined as the minimal normalized expression level across all samples for miRNAs with unreliable Ct values above Ct 31. Flooring level was determined from normalized absolute expression values ($AE_{norm}$) for miRNAs with Ct value greater than cut off as follows:

$$FL = \min_{C_t \leq cutoff} (AE_{norm})$$

All normalized AE values that were less than the flooring level were set equal to flooring level to calculate miRNA fold changes and insure no overestimation of expression differences.

In addition to using TLDA technical replicates, % false positive (false positive AE−) miRNAs detected within specific Ct ranges beginning cycle 19 up to cycle 39 were used (Table 2).

TABLE 2

Summary of fold change detection with corresponding false positive rates by various Ct range in three early stage adenocarcinoma technical replicates run on three separate TLDAs.

| Ct range | Number of detected miRNAs | Replicate fold change max | % false positive AE− | |
|---|---|---|---|---|
| | | | 1.5-fold | 2-fold |
| 19-20 | 1 | 1.18 | 0% | 0% |
| 20-21 | 0 | NA | 0% | 0% |
| 21-22 | 3 | 1.27 | 0% | 0% |
| 22-23 | 0 | NA | 0% | 0% |
| 23-24 | 5 | 1.18 | 0% | 0% |
| 24-25 | 9 | 1.23 | 0% | 0% |
| 25-26 | 11 | 1.20 | 0% | 0% |
| 26-27 | 9 | 1.21 | 0% | 0% |
| 27-28 | 8 | 1.42 | 0% | 0% |
| 28-29 | 14 | 1.40 | 0% | 0% |
| 29-30 | 16 | 1.52 | 6% | 0% |
| 30-31 | 11 | 1.45 | 0% | 0% |
| 31-32 | 14 | 2.42 | 29% | 14% |
| 32-33 | 17 | 3.47 | 65% | 41% |
| 33-34 | 10 | 2.58 | 70% | 20% |
| 34-35 | 13 | 4.77 | 92% | 85% |
| 35-36 | 12 | 5.33 | 92% | 83% |
| 36-37 | 6 | 9.76 | 100% | 100% |
| 37-38 | 5 | 7.65 | 100% | 100% |
| 38-39 | 10 | 46.43 | 90% | 90% |

Abbreviations used: fold change max=The largest actual fold change detected between triplicate TLDAs; false positive AE−=false positive; NA—not applicable.

Fold changes (1.5- and 2-fold changes) can be reliably detected with 0-6% false positive AE− up to cycle 31, while % false positive AE− sharply increases above Ct 31.

To determine whether more miRNAs could be detected if input RNA was increased up to 100 ng as the recommended range is 10-100 ng per RT, the same early stage squamous cell carcinoma pooled peripheral blood mononuclear cells sample was run on TLDA with 50 and 100 ng input RNA and miRNA expression was compared. Twenty-six (26) more miRNAs could be detected in 100 ng peripheral blood mononuclear cells pool, and the normalized cycle difference, which was calculated as RNU-corrected cycle difference per miRNA between 50 and 100 ng samples, increased tremendously with PCR cycle miRNA.

Example 2: miRNA Expression in Pooled RNA Samples

To determine whether differences in miRNA expression could be also be detected in peripheral blood mononuclear cells RNA from surgical candidates with early stage non-small cell lung cancer as compared to patients with smoking-related chronic obstructive pulmonary disease, smokers and never smokers, pooled RNAs from patients (all ex-smokers) with stage I+II lung adenocarcinoma (early stage adenocarcinoma) or lung squamous cell carcinoma (early stage squamous cell carcinoma) were analyzed with three different control groups (chronic obstructive pulmonary disease, S, NS) on the TLDAs. Each pooled RNA consisted of 6 individuals described in Table 3.

TABLE 3

Clinical and demographic profiles of non-small cell lung cancer patients and controls used on TLDAs.

| TLDA PBMC pool (n = 6) | Gender M/F | Race W | Race Other | Age* | Pack-Years* | Smoking History Yrs tobacco-free** | State T | State N | State Mt |
|---|---|---|---|---|---|---|---|---|---|
| early stage AC | 2/4 | 5 | 1 | 67 | 45 | 1 ÷ 41 | 2 | 2 | 0 |
| early stage SCC | 3/3 | 5 | 1 | 73 | 61 | 1 ÷ 26 | 2 | 2 | 0 |
| COPD | 2/4 | 2 | 4 | 64 | 57 | 4 ÷ 18 | 0 | 0 | 0 |
| Smoker | 1/5 | 2 | 4 | 49 | 22 | NA | 0 | 0 | 0 |
| Non-smoker | 5/1 | 2 | 4 | 48 | 0 | NA | 0 | 0 | 0 |

Abbreviations used: non-small cell lung cancer—non-small cell lung cancer; early stage adenocarcinoma—early (stage I + II) adenocarcinoma; early stage squamous cell carcinoma—early (stage I + II) squamous cell carcinoma; chronic obstructive pulmonary disease—chronic obstructive pulmonary disease; S—smoker; NS—never smoker; F—female; M—male; W—white; T—tumor; N—lymph node; Mt—metastasis; NA—not applicable;
*average is shown;
**range (min ÷ max) is shown.

It was determined that 268 out of 365 miRNAs on the array were not expressed at detectable levels (Ct<31) in any of the 6 RNA pools tested. Seventy eight miRNAs were detected in all pooled peripheral blood mononuclear cells samples, although not necessarily at the same levels. A total of 43 miRNAs were found to change 2-fold or more between any two of the pooled samples. Clustering of the 43 miRNAs (Table 1 and FIG. 3) showed that the S and NS pools were more closely related and the chronic obstructive pulmonary disease and early stage squamous cell carcinoma samples were most different among all the samples. Pooled peripheral blood mononuclear cells RNA from patients with late stage (III+IV) non-small cell lung cancer exhibited an even higher number than chronic obstructive pulmonary disease of miRNAs detected (total 104, not shown), and was used for control purposes only.

Figure 5:
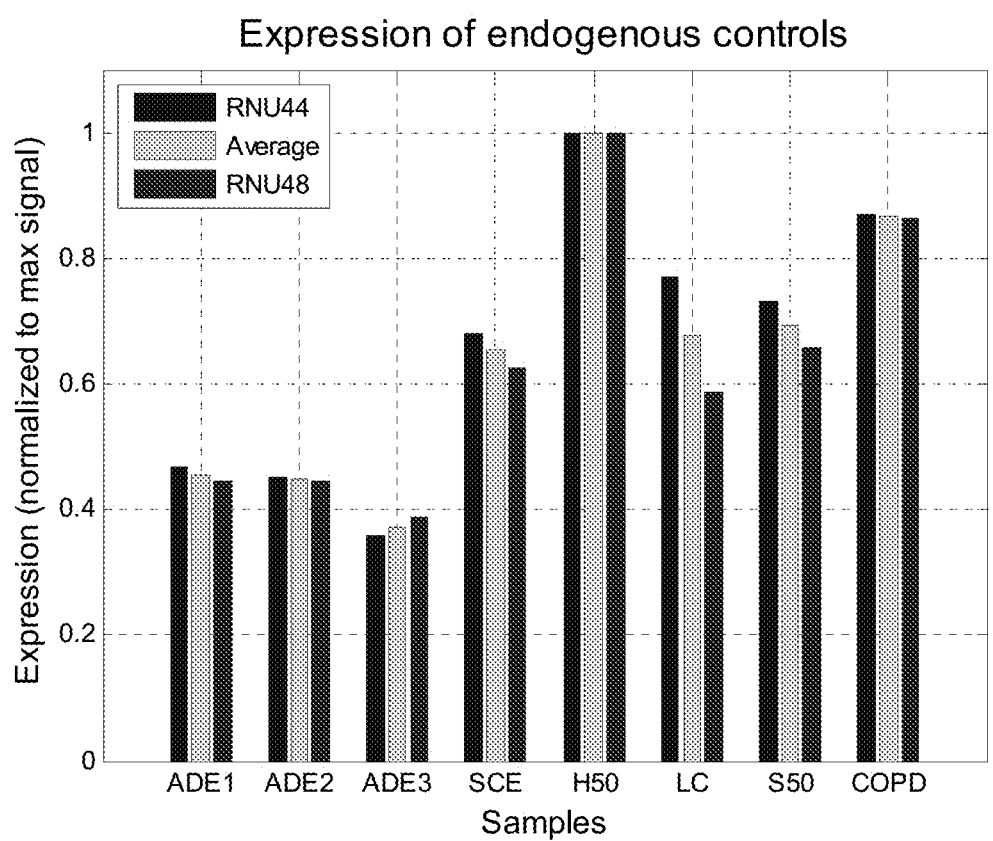
FIG. 5 is a bar graph showing that the expression of endogenous controls on TLDA is consistent within every sample tested and can be used for normalization. The graph plots RNU44 and RNU48 absolute expression values (AE) across 6 pooled PBMC samples (50 ng). AC-E sample was run on 3 different TLDAs and thus represented 3 times; LC (late stage III and IV) lung cancer sample was run as a positive control.
Figure 6A:
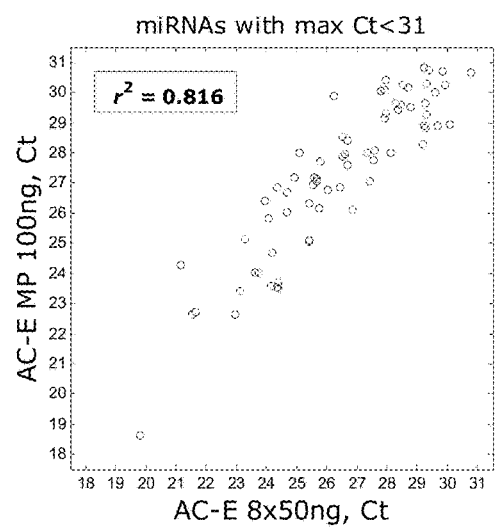
FIG. 6A is a Spearman correlation analyses of AC-E samples when 48-plex and mega-plex RT primers were used during reverse transcription step. Data was normalized using average expression of RNU44 and RNU48. miRNA expression profiles were detected using 8 RT primer pools (48-plex) and 1 RT primer pool (450-plex) protocols, and are highly correlated.
Figure 6B:
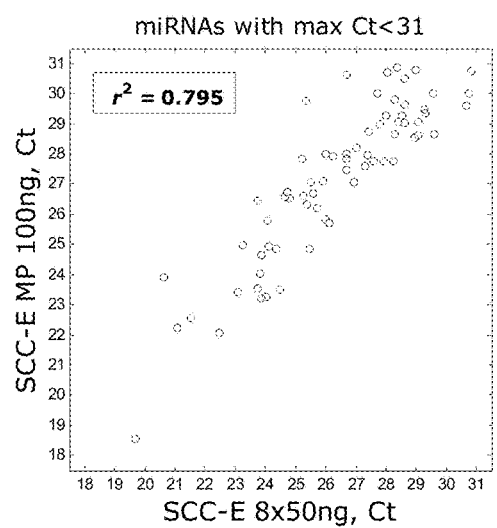
FIG. 6B is a Spearman correlation analyses of SCC-E samples when 48-plex and mega-plex RT primers were used during reverse transcription step, as described for FIG. 6A.
Figure 7A:
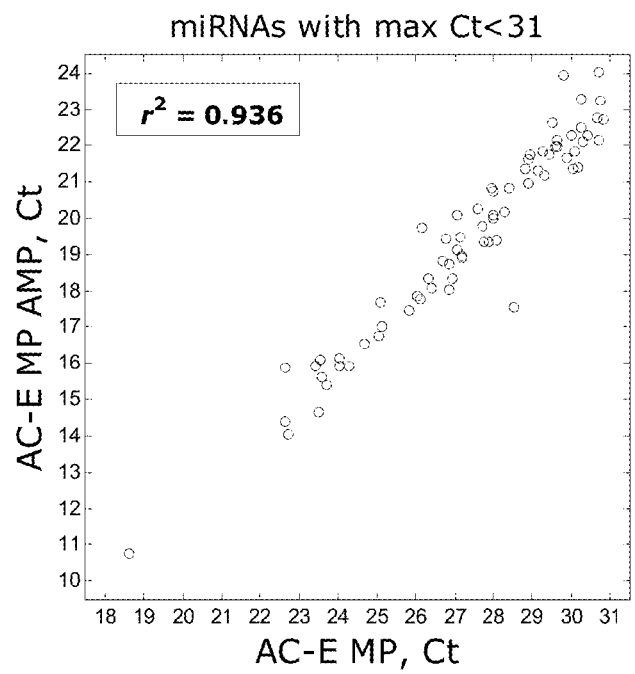
FIG. 7A is a Spearman correlation analyses of AC-E samples when miRNA expression was compared for only mega-plex (450 miRNA) RT pool with and without preamplification. Data was normalized using average expression of RNU44 and RNU48. Pre-amplification procedure substantially increased the number of detected miRNAs but did not affect overall miRNA expression.
Figure 7B:
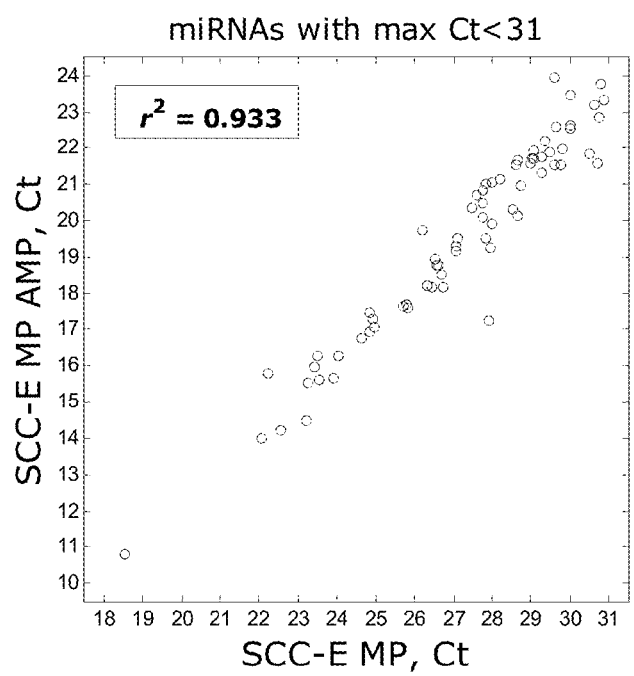
FIG. 7B is a Spearman correlation analyses of SCC-E samples using the same procedure as described for FIG. 7A.

To determine the miRNA candidates to be validated on individual assays, the level of change in expression that could be detected with good accuracy and sensitivity was assessed. As reported above, fold changes of 1.5 fold or greater could be detected on the TLDA with a false positive rate less than 6% for Ct values below 31 but increased to 30% for Ct between 31 and 32. To minimize false positives the criteria for differential expression was set at a fold change 2.0 or greater and Ct below 31. Out of the 43 miRNAs differentially expressed between any 2 samples (FIG. 5), 6 miRNAs (let-7a, let-7d, miR-142-5p, miR-148a, miR-221, and miR-328) were identified that had Ct values<31 and fold change>2 (Table 4). The expected false positive AE− rate at these fold change and Ct parameters is <10%.

TABLE 4 miRNA candidates selected on TLDA validated using single TaqMan ® miRNA assays.

| | More than 2-fold change in at least one comparison with NSCLC | |
|---|---|---|
| miRNA | COPD vs. early stage AC | COPD vs. early stage SCC |
| let-7a | 1.99 | 2.66 |
| let-7d | 1.95 | 3.02 |
| miR-142-5p | 3.38 | 7.0 |
| miR-221 | 2.34 | 4.42 |
| miR-148a | 1.92 | 3.55 |
| miR-328 | 2.31 | 4.96 |

Abbreviations used:
COPD—chronic obstructive pulmonary disease;
NSCLC—non-small cell lung cancer;
early stage AC—early (stage I + II) adenocarcinoma;
early stage SCC—early (stage I + II) squamous cell carcinoma.

To validate miRNAs selected on RNA pools on new samples, single TLDA miRNA assays were conducted for the 6 miRNAs of Table 4 using RNA from 10 or more individuals per group—patients and controls—that were not included in the peripheral blood mononuclear cells pools assayed on the previous TLDAs. In addition the same miRNA candidates on 10 samples from current and never smokers were analyzed.

Four (let-7a, let-7d, miR-221, miR-148a) out of the six miRNAs tested were significantly different in individual patient samples for chronic obstructive pulmonary disease vs. early stage squamous cell carcinoma and two (let-7a, miR-142-5p) miRNAs for chronic obstructive pulmonary disease vs. early stage adenocarcinoma (Table 5).

TABLE 5

Comparison of TLDA-derived miRNA expression obtained on pooled peripheral blood mononuclear cells samples with individual patient samples run using single TaqMan ® miRNA assays.

| Symbol Symbol | COPD/AC Ratio | COPD/SCC ratio | COPD/AC P value | COPD/LSCC P value |
|---|---|---|---|---|
| let-7a | | | | |
| Pooled | 1.99 | 2.66 | | |
| Ind. new | 1.26 | 1.56 | 0.385 | 0.121 |
| let-7d | | | | |
| Pooled | 1.95 | 3.02 | | |
| Ind. new | 1.37 | 1.57 | 0.104 | 0.140 |
| miR-221 | | | | |
| Pooled | 2.24 | 4.42 | | |
| Ind. new | 2.05 | 2.53 | 0.104 | 0.026 |
| miR-142-5p | | | | |
| Pooled | 3.38 | 7.00 | | |
| Ind. new | 2.22 | 1.40 | 0.026 | 0.571 |

TABLE 5-continued

Comparison of TLDA-derived miRNA expression obtained on pooled peripheral blood mononuclear cells samples with individual patient samples run using single TaqMan ® miRNA assays.

| Symbol Symbol | COPD/AC Ratio | COPD/SCC ratio | COPD/AC P value | COPD/LSCC P value |
|---|---|---|---|---|
| miR-328 | | | | |
| Pooled | 2.31 | 4.96 | | |
| Ind. new | 1.41 | 1.40 | 0.121 | 0.473 |
| miR-148a | | | | |
| Pooled | 1.92 | 3.55 | | |
| Ind. new | 1.19 | 2.17 | 0.791 | 0.026 |

P values were calculated using Mann-Whitney U test. Pooled groups contained combined total RNA from 6 individuals each and were run on TLDA. Individual mixed (Ind. Mixed) groups contained 10 patients partly new and partly from TLDA pool (see text for details). Individual new (Ind. New) groups contained 10 completely new patient samples. See FIGS. 4A-4D. When expression of the candidate miRNAs in the independent samples from chronic obstructive pulmonary disease, AC and LSCC patients were compared by single TaqMan® assays (Table 5), the direction of change in the individual assays was the same for all 6 samples, although ratios are lower than detected on the TLDAs. For 3 out 6 candidate miRNAs (miR-221, miR-142-5p and miR-148a) the result was statistically significant in one of the 2 comparisons. The normalized expression of 4 significant miRNA candidates tested on all five groups including smokers (S) and never smokers (NS) are shown in FIGS. 4A-4D. Although let7d was not informative for the comparison of chronic obstructive pulmonary disease with non-small cell lung cancer, it is significantly different between chronic obstructive pulmonary disease and "healthy" smokers as well as never smokers.

Moreover, with 100% new individual patient samples miR-148a became a stronger candidate allowing differentiation between 2 early non-small cell lung cancer types: adenocarcinoma and squamous cell carcinoma. In addition, let-7d and miR-221 separated well chronic obstructive pulmonary disease (mainly former smokers) from either current smokers (S) and/or never smokers (NS), and miR-142-5p was expressed at significantly lower levels in early adenocarcinoma (early stage adenocarcinoma) patients compared to diseased and non-diseased controls: chronic obstructive pulmonary disease, smoker and non smoker. Even though TLDA-derived miR-142-5p expression was not confirmed on 100% new early stage squamous cell carcinoma individual patient samples, there was a tendency to follow the early stage adenocarcinoma pattern. MiR-142-5p was expressed at significantly lower levels in AC-E patients compared to all control groups COPD, S and NS as was found with the pooled comparisons. However the high differential expression detected between the pooled COPD and SCC samples was not confirmed by the individual assays. There was a general tendency of higher expression in the COPD samples but the difference did not reach statistical significance.

Additional studies are ongoing that use a single reaction mega-plex RT primer pool (450 miRNAs) and a newly developed miRNA pre-amplification that permit studies with small amounts of RNA from highly limited clinical samples.

Example 3: Differential Expression of miRNAs in NSCLC Patients after Tumor Removal There is a complex of direct-mRNA/TF upstream/miRNA regulations implicated by the presence of cancer (or tumor) present. A strong signature of cancer is observed in blood immune cells, which mostly downregulates immune functions. Multiple miRNAs target key nodes of immune processes. There is a trend of upregulation of miRNAs in biological, e.g., PBMC, samples of subjects with NSCLC before surgical resection of tumor tissue (PRE-) and after surgery (POST-). Specifically 5 miRNAs are highly significantly changed.

MicroRNA transcription was analyzed on a subset of patient samples, using Illumina bead arrays. PBMC from the 18 patient pairs were collected. Of these 18 patients, 10 were diagnosed with adenocarcinoma, 6 were diagnosed with LSCC and 2 were diagnosed as unclassified NSCLC. Times of sample collection post-surgery ranged from 1 to 5 months with majority of samples (10) being taken 2 months after surgery and only 2 samples taken at 1, 3, 4 and 5 months post-surgery. All samples were collected before any additional therapy was started. Blood samples were drawn in two "CPT" tubes (BD). PBMC were isolated within 90 minutes of blood draw, washed in PBS, transferred into RNA Later (Ambion) and then stored at 4° C. overnight before transfer to −80° C. Extracted RNA was used for further processing.

Illumina microRNA expression profiling platform was used to study changes in expression levels of microRNAs in PBMC taken post surgery in 11 of 18 patients. RNA purification was carried out using TriReagent Molecular Research) as recommended and controlled for quality using the Bioanalyzer. Only samples with 28S/16S ratios>0.75 were used for further studies. A constant amount (500 ng) of total RNA was amplified as recommended by Illumina. Samples were hybridized to the human Illumina MicroRNA v2 (Universal 12 Beadchip 1536 bead type) Sentrix Beadchip Array. Illumina BeadStudio v.3.0 software was used to export expression levels and detection p-values for each probe of each sample. Arrays were normalized to $95^{th}$ percentile of overall slide expression and filtered to remove non-informative miRNA probes. A probe was called non-informative if it had expression signals with detection p-value>0.05 in all samples or if it had expression signals less than 2 average background levels in all samples.

miRNA expression data for 11 pre/post pairs of samples was tested for differential expression using two-tail pairwise t-test with significance set to p-value<0.05 unless stated otherwise. False Discovery Rate was calculated according to Storey JD procedure (Storey Tibshirani 2003). SVM-RFE. List of ranked genes was received using linear kernel SVM-RFE[22] with 10-fold 10 resampling cross validation. Each cross-validation iteration started with 1000 top significant by t-test genes and the number of genes was reduced by 10% at each feature elimination step based on gene SVM-scores. Final ranking of the genes was done by Borda count procedure. Heatmaps. Heatmap for a list of genes is composed using 2-way hierarchical clustering using Euclidean distance to cluster samples/conditions and Spearman correlation distance to cluster genes. Pathway and functional analysis was carried out with Ingenuity Pathways Analysis software using Ingenuity Core Analysis (IPA 6.0, Ingenuity® Systems) with Benjamini-Hochberg multiple testing corrected p-value<0.05 as a significance threshold.

Enrichments of Gene Ontology (GO) terms, KEGG and BIOCARTA pathways along with Swiss-Prot, INTERPRO and SMART keywords in a gene list was done with DAVID software. Results were filtered to satisfy FDR<5% and Fold Enrichment>1.5 criteria. Putative miRNA target genes. Computationally predicted target genes for a miRNA were derived from results of miRanda target scanner software runs as provided by Sanger (United Kingdom; website indicated by microrna.sanger.ac.uk) or Sloan-Kettering (website indicated by microrna.org) databases. Overlap with gene expression data was done using Entrez Gene IDs and a computationally predicted target gene was called a putative miRNA target if it was significantly downregulated in PRE surgery samples as assessed by one-tail paired t-test with significance threshold p-value<0.1.

Q-PCR validation of array results was carried out using the ABI TaqMan System as recommended, in an ABI 7900HT PCR System. Each sample was analyzed in duplicate and samples with CVs between replicates that were more than 0.5 delta Ct were repeated.

From 1146 expressed probes on the array, 643 differentially expressed miRNAs met the selection criteria of being expressed in at least one sample. Of the 643 miRNAs detected, 108 were putative miRNAs that were predicted by parallel sequencing. The rest of the detected probes targeted 443 unique miRNAs with 92 minor miR* forms. Forty-six (46) known miRNAs (paired t-test, p-value<0.05) were differentially expressed between pre- and post-surgery samples (FDR of 42%). Out of those 46 miRNAs, 42 (91%) showed upregulation in samples taken pre surgery.

Figure 8:
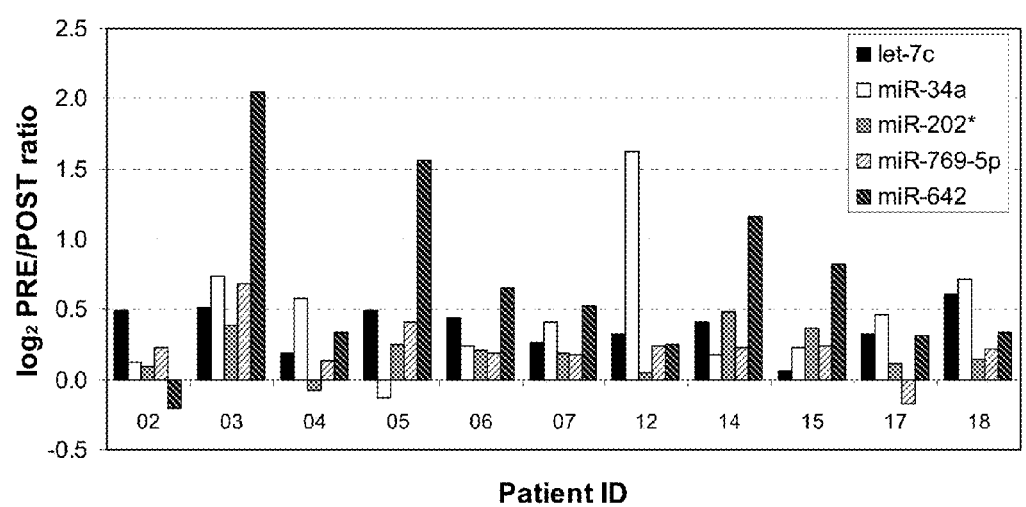
FIG. 8 is a bar graph showing pre-surgery (PRE)/post-surgery (POST) ratios for miRNAs with false discovery rate (FDR)<15%. The data is presented in log scale to accent patients where miRNAs did not show upregulation. The numbers indicate the specific patient. Black square represents miR-let-7c; white square represents miR-34a; gray square represents mIR-202*, white cross-hatched square represents mIR-769-5p and dark cross-hatched square represents miR-642.

Universally altered expression was detected of five miRNAs let-7c, miR-34a, miR-202 in its minor form (hsa-miR-202*) and miR-769-5p in the pre compared to the post-surgery samples. These five miRNAs satisfied the criteria of a p-value<0.002 and a FDR<15%. All were upregulated in pre-surgery samples. Magnitudes of the changes in each patient in those miRNAs are presented in FIG. 8. As can be seen from the figure, let-7c is shows upregulation in all 11 tested patients with median upregulation of 33% and a range from 4% to 52%. The other miRNAs show upregulation in 10 of the 11 patients (values below zero in FIG. 3) with median upregulation in the rest of the patients as follows: 35% for miR-34a, 14% for miR-202*, 17% for miR-769-5p and 51% for miR-642. Only patients 2, 4, 5 and 17, all adenocarcinomas, have one of the 5 miRNAs which does not follow the general trend in the other 10 samples and this miRNA was different for each of these patients.

These five miRNAs may have common regulators as identified by transcription factor binding site (TFBS) analysis. These 5 miRNAs have predicted targets involved in immune functions. It is theorized that the targets are generally downstream pathway targets, such as kinases and transcription factors). The Toll-like receptor (TLR) pathway is significantly targeted by those miRNAs. Expression of these miRNAs is negatively correlated with subset of genes that are differentially expressed between pre and post surgery samples. All of these miRNAs target downstream genes of TLR signaling pathway. The tumor presence induces a downregulation of TLR signaling pathways through miRNA targeting various key molecules in these pathways.

Each and every patent, patent application, and publication, including websites cited throughout the disclosure, and U.S. provisional application No. 61/112,744 is expressly incorporated herein by reference in its entirety. While this invention has been disclosed with reference to specific embodiments, it is apparent that other embodiments and variations of this invention are devised by others skilled in the art without departing from the true spirit and scope of the invention. The appended claims include such embodiments and equivalent variations.

The invention claimed is:

1. A method of treating a mammalian subject having a lung nodule comprising (a) distinguishing between chronic obstruction pulmonary disease (COPD) and non-small cell lung cancer (NSCLC) in the mammalian subject by a method comprising:

obtaining a biological sample selected from whole blood, peripheral blood mononuclear cells, plasma and serum from the subject;

measuring, via quantitation with real-time PCR or qRT PCR, expression of at least two of the subject's miRNA levels, wherein the at least two of the subject's miRNAs are selected from the set consisting of hsa-miR-148a, hsa-miR-142-5p, hsa-miR-221, hsa-miR-let-7d, hsa-miR-let-7a, hsa-miR-328;

diagnosing a non-small cell lung cancer (NSCLC) in a mammalian subject when a downregulation in said miRNA levels is detected as compared to a reference miRNA standard, wherein the reference miRNA standard is a reference subject or reference population selected from the group consisting of (a) a reference human subject or population having COPD, (b) a reference human subject or population who are healthy and have never smoked, and (c) a reference human subject or population who are former smokers or current smokers with no disease; and (b) treating the NSCLC by surgical resection of the nodule.

2. The method according to claim 1, wherein the reference miRNA standard is a mean, an average, a numerical mean or range of numerical means, a numerical pattern, a graphical pattern or an miRNA expression profile derived from a reference subject or reference population.

3. The method according to claim 2, wherein said NSCLC is squamous cell carcinoma or adenocarcinoma.

* * * * *

SEQUENCE LISTING

```
<160> NUMBER OF SEQ ID NOS: 48

<210> SEQ ID NO 1
<211> LENGTH: 20
<212> TYPE: RNA
<213> ORGANISM: Homo sapiens

<400> SEQUENCE: 1
cauaaaguag aaagcacuac                                                    20

<210> SEQ ID NO 2
<211> LENGTH: 22
<212> TYPE: RNA
<213> ORGANISM: Homo sapiens

<400> SEQUENCE: 2
cuggcccucu cugcccuucc gu                                                 22

<210> SEQ ID NO 3
<211> LENGTH: 22
<212> TYPE: RNA
<213> ORGANISM: Homo sapiens

<400> SEQUENCE: 3
ucggauccgu cugagcuugg cu                                                 22

<210> SEQ ID NO 4
<211> LENGTH: 23
<212> TYPE: RNA
```

<213> ORGANISM: Homo sapiens

<400> SEQUENCE: 4
agcuacauug ucugcugggu uuc                                    23

<210> SEQ ID NO 5
<211> LENGTH: 22
<212> TYPE: RNA
<213> ORGANISM: Homo sapiens

<400> SEQUENCE: 5
ucagugcauc acagaacuuu gu                                     22

<210> SEQ ID NO 6
<211> LENGTH: 22
<212> TYPE: RNA
<213> ORGANISM: Homo sapiens

<400> SEQUENCE: 6
ucagugcacu acagaacuuu gu                                     22

<210> SEQ ID NO 7
<211> LENGTH: 22
<212> TYPE: RNA
<213> ORGANISM: Homo sapiens

<400> SEQUENCE: 7
acuagacuga agcuccuuga gg                                     22

<210> SEQ ID NO 8
<211> LENGTH: 23
<212> TYPE: RNA
<213> ORGANISM: Homo sapiens

<400> SEQUENCE: 8
agcagcauug uacagggcua uga                                    23

<210> SEQ ID NO 9
<211> LENGTH: 23
<212> TYPE: RNA
<213> ORGANISM: Homo sapiens

<400> SEQUENCE: 9
ucaagagcaa uaacgaaaaa ugu                                    23

<210> SEQ ID NO 10
<211> LENGTH: 21
<212> TYPE: RNA
<213> ORGANISM: Homo sapiens

<400> SEQUENCE: 10
ucguaccgug aguaauaaug c                                      21

<210> SEQ ID NO 11
<211> LENGTH: 22
<212> TYPE: RNA
<213> ORGANISM: Homo sapiens

<400> SEQUENCE: 11
uaaggugcau cuagugcaga ua                                     22

<210> SEQ ID NO 12
<211> LENGTH: 21

```
<212> TYPE: RNA
<213> ORGANISM: Homo sapiens

<400> SEQUENCE: 12
agagguagua gguugcauag u                                              21

<210> SEQ ID NO 13
<211> LENGTH: 23
<212> TYPE: RNA
<213> ORGANISM: Homo sapiens

<400> SEQUENCE: 13
caaagaauuc uccuuuggg cuu                                             23

<210> SEQ ID NO 14
<211> LENGTH: 23
<212> TYPE: RNA
<213> ORGANISM: Homo sapiens

<400> SEQUENCE: 14
aaugacacga ucacucccgu uga                                            23

<210> SEQ ID NO 15
<211> LENGTH: 21
<212> TYPE: RNA
<213> ORGANISM: Homo sapiens

<400> SEQUENCE: 15
gccccugggc cuauccuaga a                                              21

<210> SEQ ID NO 16
<211> LENGTH: 24
<212> TYPE: RNA
<213> ORGANISM: Homo sapiens

<400> SEQUENCE: 16
caaagugcuu acagugcagg uagu                                           24

<210> SEQ ID NO 17
<211> LENGTH: 22
<212> TYPE: RNA
<213> ORGANISM: Homo sapiens

<400> SEQUENCE: 17
uagcagcaca ucaugguuua ca                                             22

<210> SEQ ID NO 18
<211> LENGTH: 22
<212> TYPE: RNA
<213> ORGANISM: Homo sapiens

<400> SEQUENCE: 18
ugagguagua gguuguauag uu                                             22

<210> SEQ ID NO 19
<211> LENGTH: 23
<212> TYPE: RNA
<213> ORGANISM: Homo sapiens

<400> SEQUENCE: 19
aaaccguuac cauuacugag uuu                                            23

<210> SEQ ID NO 20
```

-continued

```
<211> LENGTH: 21
<212> TYPE: RNA
<213> ORGANISM: Homo sapiens

<400> SEQUENCE: 20
ggcaagaugc uggcauagcu g                                              21

<210> SEQ ID NO 21
<211> LENGTH: 22
<212> TYPE: RNA
<213> ORGANISM: Homo sapiens

<400> SEQUENCE: 21
uccuguacug agcugccccg ag                                             22

<210> SEQ ID NO 22
<211> LENGTH: 23
<212> TYPE: RNA
<213> ORGANISM: Homo sapiens

<400> SEQUENCE: 22
caaagugcuc auagugcagg uag                                            23

<210> SEQ ID NO 23
<211> LENGTH: 22
<212> TYPE: RNA
<213> ORGANISM: Homo sapiens

<400> SEQUENCE: 23
cuuucagucg gauguuuaca gc                                             22

<210> SEQ ID NO 24
<211> LENGTH: 22
<212> TYPE: RNA
<213> ORGANISM: Homo sapiens

<400> SEQUENCE: 24
agcucggucu gaggccccuc ag                                             22

<210> SEQ ID NO 25
<211> LENGTH: 22
<212> TYPE: RNA
<213> ORGANISM: Homo sapiens

<400> SEQUENCE: 25
uacaguaguc ugcacauugg uu                                             22

<210> SEQ ID NO 26
<211> LENGTH: 22
<212> TYPE: RNA
<213> ORGANISM: Homo sapiens

<400> SEQUENCE: 26
aaagugcugu ucgugcaggu ag                                             22

<210> SEQ ID NO 27
<211> LENGTH: 22
<212> TYPE: RNA
<213> ORGANISM: Homo sapiens

<400> SEQUENCE: 27
aaggagcuca cagucuauug ag                                             22
```

-continued

```
<210> SEQ ID NO 28
<211> LENGTH: 22
<212> TYPE: RNA
<213> ORGANISM: Homo sapiens

<400> SEQUENCE: 28
uagcuuauca gacugauguu ga                                                  22

<210> SEQ ID NO 29
<211> LENGTH: 24
<212> TYPE: RNA
<213> ORGANISM: Homo sapiens

<400> SEQUENCE: 29
agcuacaucu ggcuacuggg ucuc                                                24

<210> SEQ ID NO 30
<211> LENGTH: 20
<212> TYPE: RNA
<213> ORGANISM: Homo sapiens

<400> SEQUENCE: 30
uguaaacauc cuugacugga                                                     20

<210> SEQ ID NO 31
<211> LENGTH: 25
<212> TYPE: RNA
<213> ORGANISM: Homo sapiens

<400> SEQUENCE: 31
cccaucuggg guggccugug acuuu                                               25

<210> SEQ ID NO 32
<211> LENGTH: 23
<212> TYPE: RNA
<213> ORGANISM: Homo sapiens

<400> SEQUENCE: 32
uccgucucag uuacuuuaua gcc                                                 23

<210> SEQ ID NO 33
<211> LENGTH: 21
<212> TYPE: RNA
<213> ORGANISM: Homo sapiens

<400> SEQUENCE: 33
cauuauuacu uuggguacgc g                                                   21

<210> SEQ ID NO 34
<211> LENGTH: 22
<212> TYPE: RNA
<213> ORGANISM: Homo sapiens

<400> SEQUENCE: 34
cagugcaaug uuaaaagggc au                                                  22

<210> SEQ ID NO 35
<211> LENGTH: 22
<212> TYPE: RNA
<213> ORGANISM: Homo sapiens

<400> SEQUENCE: 35
cauugcacuu gucucggucu ga                                                  22
```

-continued

```
<210> SEQ ID NO 36
<211> LENGTH: 22
<212> TYPE: RNA
<213> ORGANISM: Homo sapiens

<400> SEQUENCE: 36
uacccauugc auaucggagu ug                                                 22

<210> SEQ ID NO 37
<211> LENGTH: 24
<212> TYPE: RNA
<213> ORGANISM: Homo sapiens

<400> SEQUENCE: 37
aacauucauu guugucggug gguu                                               24

<210> SEQ ID NO 38
<211> LENGTH: 23
<212> TYPE: RNA
<213> ORGANISM: Homo sapiens

<400> SEQUENCE: 38
ucccugagac ccuuuaaccu gug                                                23

<210> SEQ ID NO 39
<211> LENGTH: 21
<212> TYPE: RNA
<213> ORGANISM: Homo sapiens

<400> SEQUENCE: 39
uucacagugg cuaaguucug c                                                  21

<210> SEQ ID NO 40
<211> LENGTH: 22
<212> TYPE: RNA
<213> ORGANISM: Homo sapiens

<400> SEQUENCE: 40
caugccuuga guguaggacc gu                                                 22

<210> SEQ ID NO 41
<211> LENGTH: 22
<212> TYPE: RNA
<213> ORGANISM: Homo sapiens

<400> SEQUENCE: 41
uggcucaguu cagcaggaac ag                                                 22

<210> SEQ ID NO 42
<211> LENGTH: 22
<212> TYPE: RNA
<213> ORGANISM: Homo sapiens

<400> SEQUENCE: 42
aacauucauu gcugucggug gg                                                 22

<210> SEQ ID NO 43
<211> LENGTH: 22
<212> TYPE: RNA
<213> ORGANISM: Homo sapiens

<400> SEQUENCE: 43
aagcugccag uugaagaacu gu                                                 22
```

```
<210> SEQ ID NO 44
<211> LENGTH: 84
<212> TYPE: RNA
<213> ORGANISM: Homo sapiens

<400> SEQUENCE: 44
gcauccgggu ugagguagua gguuguaugg uuuagaguua cacccuggga guuaacugua        60
caaccuucua gcuuuccuug gagc                                              84

<210> SEQ ID NO 45
<211> LENGTH: 110
<212> TYPE: RNA
<213> ORGANISM: Homo sapiens

<400> SEQUENCE: 45
ggccagcugu gaguguuucu uuggcagugu cuuagcuggu uguugugagc aauaguaagg        60
aagcaaucag caaguauacu gcccuagaag ugcugcacgu uguggggccc                  110

<210> SEQ ID NO 46
<211> LENGTH: 110
<212> TYPE: RNA
<213> ORGANISM: Homo sapiens

<400> SEQUENCE: 46
cgccucagag ccgcccgccg uuccuuuuuc cuaugcauau acuucuuuga ggaucuggcc        60
uaaagaggua uagggcaugg gaaaacgggg cggucggguc cuccccagcg                  110

<210> SEQ ID NO 47
<211> LENGTH: 22
<212> TYPE: RNA
<213> ORGANISM: Homo sapiens

<400> SEQUENCE: 47
ugagaccucu ggguucugag cu                                                22

<210> SEQ ID NO 48
<211> LENGTH: 97
<212> TYPE: RNA
<213> ORGANISM: Homo sapiens

<400> SEQUENCE: 48
aucugaguug ggaggguccc ucuccaaaug ugucuugggg uggggauca agacacauuu        60 ggagagggaa ccucccaacu cggccucugc caucauu                               97
```